United States Patent [19]

Seto et al.

[11] Patent Number: 5,294,530
[45] Date of Patent: Mar. 15, 1994

[54] SILVER HALIDE COLOR PHOTOGRAPHIC MATERIAL

[75] Inventors: Nobuo Seto; Masakazu Morigaki, both of Kanagawa, Japan

[73] Assignee: Fuji Photo Film Co., Ltd., Kanagawa, Japan

[21] Appl. No.: 883,269

[22] Filed: May 14, 1992

[30] Foreign Application Priority Data

May 17, 1991 [JP] Japan .................. 3-140738

[51] Int. Cl.$^5$ .............. G03C 7/34; G03C 7/36; G03C 7/392
[52] U.S. Cl. .................. 430/551; 430/552; 430/553; 430/556; 430/557
[58] Field of Search ............. 430/551, 604, 610, 611, 430/614, 552, 553, 556, 557

[56] References Cited

U.S. PATENT DOCUMENTS

| | | | |
|---|---|---|---|
| 3,936,305 | 2/1976 | Hiraishi et al. | 430/512 |
| 4,656,125 | 4/1987 | Renner et al. | 430/551 |
| 4,749,645 | 6/1988 | Goddard et al. | 430/551 |
| 4,782,011 | 11/1988 | Goodard et al. | 430/551 |

FOREIGN PATENT DOCUMENTS

| | | | |
|---|---|---|---|
| 50-87326 | 7/1975 | Japan . | |
| 54-70830 | 6/1979 | Japan . | |
| 2043641 | 2/1984 | Japan . | 430/551 |
| 616652 | 1/1986 | Japan . | |
| 1-137257 | 5/1989 | Japan . | |
| 1-137258 | 5/1989 | Japan . | |
| 1137254 | 5/1989 | Japan . | |
| 1-144048 | 6/1989 | Japan . | |
| 1-289952 | 11/1989 | Japan . | |
| 3142445 | 6/1991 | Japan . | 430/610 |

OTHER PUBLICATIONS

J01/144048-Abstract Jun. 6, 1989.
J01/289952-Abstract Nov. 21, 1989.

Primary Examiner—Lee C. Wright
Attorney, Agent, or Firm—Sughrue, Mion, Zinn, Macpeak & Seas

[57] ABSTRACT

A silver halide color photographic material comprising a support having thereon one or more hydrophilic colloid layers, at least one layer which is a light-sensitive silver halide emulsion layer containing in the same layer a color coupler selected from a yellow coupler and a cyan coupler and at least one anti-fading agent represented by formula (I):

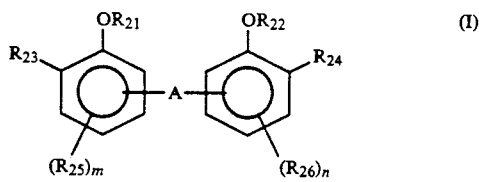

The novel anti-fading agent effectively prevents yellow and cyan dye images from fading or discoloration, and does not adversely affect other photographic properties.

15 Claims, No Drawings

SILVER HALIDE COLOR PHOTOGRAPHIC MATERIAL

FIELD OF THE INVENTION

This invention relates to a silver halide color photographic material, and more particularly to a silver halide color photographic material which provides a processed dye image which is resistant to fading and discoloration.

BACKGROUND OF THE INVENTION

Generally, a silver halide color photographic material has silver halide emulsion layers which are individually sensitive to the three primary colors of red, green and blue. A dye image is produced by a method wherein three types of color couplers in the respective emulsion layers are developed to form colors complementary to the color sensitivity of each layer, i.e., by subtractive color photography. Generally, dye images obtained by processing the silver halide color photographic material comprise an azomethine dye or an indoaniline dye formed by the reaction of the couplers with the oxidant of an aromatic primary amine color developing agent. The thus-formed color photographic images are not always stable upon exposure to light or moist heat. When the dye images are exposed to light or stored under conditions of high temperature and humidity over a long period of time, the dye images become faded or discolored, and the image quality is deteriorated.

The fading or discoloration of the images is a serious problem of prior art recording materials. Accordingly, many techniques have been proposed to solve the problem. For example, couplers which form dyes having high fastness have been developed, anti-fading agents have been employed, and ultraviolet light absorbents have been used to protect the images from deterioration by exposure to ultraviolet light.

Particularly, anti-fading agents remarkably prevent deterioration of the images. For example, it is known that the addition to the photographic material of hydroquinones, hindered phenols, catechols, gallic esters, aminophenols, hindered amines, chromanols, indanes, and ethers or esters obtained by silylating, acylating or alkylating the phenolic hydroxyl group of these compounds, and metal complexes prevents image deterioration.

Although the above noted anti-fading agents are effective as fading or discoloration inhibitors for dye images, these compounds are insufficient for meeting the demand for higher image quality. In addition, these compounds are considered to be poor color photographic additives on the whole. Particularly, addition of these prior art anti-fading agents results in a change in hue, generation of fog, dispersion failure, or the formation of crystallites after coating of the emulsion.

JP-A-61-6652 (the term "JP-A" as used herein means an "unexamined published Japanese patent application") and JP-A-1-137258 propose the use of bisphenol compounds having a specific structure to prevent dye images obtained from yellow couplers from fading or discoloration. Furthermore, JP-A-54-70830 proposes the use of bisphenol compounds having a specific structure and dialkoxybenezene compounds in combination to prevent discoloration.

However, these compounds either do not effectively prevent fading, or cause considerable staining of the white background portions. Accordingly, adequate improvement of the fastness of the dye images is not obtained. Furthermore, some of these compounds cause a change in hue. JP-A-62-262047 discloses the use of bisphenol compounds having improved properties with regard to the solution of these problems; however, the compounds of JP-A-62-262047 still do not sufficiently improve the fastness of the dye images.

Furthermore, JP-A-52-150630, JP-A-53-108428, JP-A-55-6321 and JP-A-61-86750 propose the use of specific aminophenol compounds to prevent the dye images from fading or discoloration.

However, the specific aminophenol compounds do not sufficiently improve the fastness of the dye images. For example, these compounds either do not effectively prevent fading, or cause considerable staining of the white background portions. Furthermore, some of these compounds cause color formation (hereinafter referred to as fogging) in unexposed areas, or interfere with the color formation of the couplers. Namely, some of the aminophenol compounds adversely affect photographic characteristics.

Accordingly, there is a demand to provide a method which prevents the fading or discoloration of images without adversely affecting photographic characteristics.

SUMMARY OF THE INVENTION

An object of the present invention is to provide a silver halide color photographic material which provides a color image which is not discolored over a long period of time and has good preservability.

Another object of the present invention is to provide a silver halide color photographic material containing a novel anti-fading agent which effectively prevents yellow dye images from fading or discoloration, which anti-fading agent does not form crystallites after coating, and which anti-fading agent does not cause a change in hue or interfere with the color formation of the couplers or cause fogging.

Still another object of the present invention is to provide a silver halide color photographic material containing an anti-fading agent having excellent solubility in high-boiling organic solvents, etc., which anti-fading agent does not form crystallites before or after coating and does not interfere with other photographic additives.

A further object of the present invention is to provide a silver halide color photographic material containing an anti-fading agent which does not adversely affect photographic characteristics, and which anti-fading agent effectively prevents fading of yellow dye images and/or cyan dye images and does not color unexposed areas.

After extensive investigations, the present inventors have discovered that the above objects of the present invention are achieved by providing a silver halide color photographic material comprising a support having thereon one or more hydrophilic colloid layers, at least one layer of which is a light-sensitive silver halide emulsion layer containing in the same layer a color coupler selected from the group consisting of a yellow coupler and a cyan coupler and at least one compound represented by the formula (I):

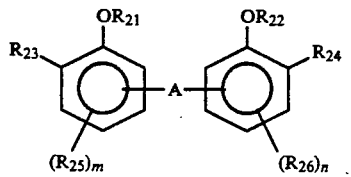

In formula (I), A represents a single bond, —O—, —S(O)$_p$—, —N(R$_{27}$)— or —(C(R$_{28}$)(R$_{29}$)T)—; R$_{21}$ and R$_{22}$ each represents a hydrogen atom, an aliphatic group, —C(O)— R$_{33}$, —S(O)$_2$—R$_{33}$, —P(R$_{33}$)(R$_{34}$) or —P(O)(R$_{33}$)(R$_{34}$); R$_{23}$ and R$_{24}$ each represents an aromatic group, a heterocyclic group, an aromatic oxy group, an aromatic thio group, an aliphatic acyl group, an aromatic acyl group, an aliphatic oxycarbonyl group, an aromatic oxycarbonyl group, an aliphatic acylamino group, an aromatic acylamino group, an aliphatic sulfonamido group, an aromatic sulfonamido group, an imido group, an aliphatic acyloxy group, an aromatic acyloxy group, an aliphatic sulfonyl group, an aromatic sulfonyl group, an aliphatic sulfonyloxy group, an aromatic sulfonyloxy group, an aliphatic oxycarbonylamino group, an aromatic oxycarbonylamino group, a carbamoylamino group, a sulfamoylamino group, a carbamoyl group, a sulfamoyl group or a group represented by the following formula:

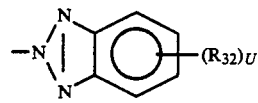

wherein R$_{25}$ and R$_{26}$ have the same meaning as R$_{23}$, or each represents an aliphatic group; and m and n each represents an integer of 1 to 3. When any of m and n are 2 or 3, the two or three R$_{25}$ or R$_{26}$ groups may be the same or different; R$_{21}$ and R$_{22}$, R$_{21}$ and R$_{23}$, R$_{22}$ and R$_{24}$, R$_{23}$ and R$_{25}$ or R$_{24}$ and R$_{26}$ may be combined together to form a five-membered to eight-membered ring; R$_{27}$ represents hydrogen atom, an aliphatic group, an aliphatic acyl group, an aromatic acyl group, an aliphatic sulfonyl group, an aromatic sulfonyl group, an aliphatic oxycarbonyl group or an aromatic oxycarbonyl group; R$_{28}$ and R$_{29}$ each represents a hydrogen atom, an aliphatic group or an aromatic group; R$_{32}$ has the same meaning as R$_{25}$; R$_{33}$ and R$_{34}$ each represents an aliphatic group, an aromatic group, an aliphatic oxy group or an aromatic oxy group; p and U each represents 0, 1 or 2; and T represents 1 or 2. When T is 2, the two R$_{28}$ or R$_{29}$ groups may be the same or different.

Unless otherwise indicated, the term "aliphatic group" as used herein means a C$_{1-50}$, preferably C$_{1-30}$, straight chain, branched chain or cyclic chain which may be saturated or unsaturated, such as alkyl (e.g., methyl, ethyl, butyl), alkenyl (e.g., allyl. propenyl), alkynyl (e.g., propynyl), cycloalkyl (e.g., cyclohexyl, cyclopropyl) or cycloalkenyl (e.g., cyclopropenyl). These groups may have one or more substituent groups. Unless otherwise indicated, the term "aromatic group" as used herein means a C$_{6-56}$, preferably C$_{6-36}$ aryl (e.g., phenyl, naphthyl) which may have one or more substituent groups. Unless otherwise indicated, the term "heterocyclic ring" as used herein means a C$_{1-50}$, preferably C$_{1-36}$, five-membered to eight-membered ring having one or more hetero-atoms, N, O, S and P, as one or more members of the ring (e.g., N-indolinyl, 2-pyridinyl, 1-piperidinyl, 2-pyrimidinyl, 2-thiazolyl, morpholino, 1-pyrazolyl, 1-piperazino, tetrazolyl, 1,3,4-thiaziazolyl, 1,3,4-oxadiazolyl, 1,3,4-triazolyl, benzimidazolyl, benzothiazolyl, imidazolyl, 1,2,3-triazole, benzotriazolyl) and includes aromatic heterocyclic rings. The ring may have one or more substituent groups.

The term "substituent group" as used herein means any group which can be attached to the above-described groups and rings. Examples of the substituent group include an aliphatic group, an aromatic group, a heterocyclic group, an aliphatic acyl group, an aromatic acyl group, an aliphatic acyloxy group, an aromatic acyloxy group, an aliphatic acylamino group, an aromatic acylamino group, an aliphatic oxy group, an aromatic oxy group, a heterocyclic oxy group, an aliphatic oxycarbonyl group, an aromatic oxycarbonyl group, a heterocyclic oxycarbonyl group, an aliphatic carbamoyl group, an aromatic carbamoyl group, an aliphatic sulfonyl group, an aromatic sulfonyl group, an aliphatic sulfamoyl group, an aromatic sulfamoyl group, an aliphatic sulfonamido group, an aromatic sulfonamido group, an aliphatic amino group, an aromatic amino group, an aliphatic sulfinyl group, an aromatic sulfinyl group, an aliphatic thio group, an aromatic thio group, an aliphatic sulfamoylamino group, an aromatic sulfamoylamino group, a mercapto group, a hydroxyl group, cyano group, a hydroxyamino group, an aliphatic sulfonyloxy group, an aromatic sulfonyloxy group, an aliphatic carbamoylamino group, an aromatic carbamoylamino group, and a halogen atom.

DETAILED DESCRIPTION OF THE INVENTION

The present invention is illustrated in detail below.

The total carbon numbers of groups and substituents are expressed herein as, for example, "C$_{1-5}$" for "a total carbon number from one to five". For example, a C$_{1-5}$ alkyl group means an alkyl group having a total carbon number from one to five.

Yellow couplers for use in the present invention in combination with the compound represented by formula (I) in the same layer may be any yellow couplers and examples are described in, for example, U.S. Pat. Nos. 3,227,554, 3,408,194, 3,894,875, 3,933,501, 3,973,968, 4,022,620, 4,057,432, 4,115,121, 4,203,768, 4,266,019, 4,314,023, 4,327,175, 4,401,752, 4,404,274, 4,420,556, 4,711,837 and 4,729,944, European Patents 30,747A, 296,793A, 313,308A and 447,969A, West German Patent 3,107,173C, JP-A-59-174839, JP-A-63-123047, and Japanese Patent Application No. 3-228500.

Yellow couplers which are preferably used in the same layer with the compounds of formula (I) according to the present invention are compounds represented by the following formula (Y).

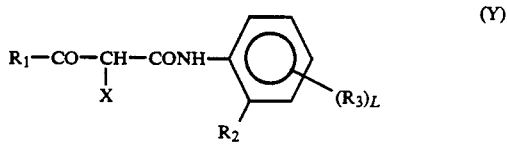

In formula (Y), R$_1$ represents a C$_{4-30}$, preferably C$_{4-10}$ tertiary alkyl group, a C$_{6-36}$, preferably C$_{6-26}$ aryl group, a substituted C$_{2-40}$, preferably C$_{2-20}$ amino group in which preferred substituents include an alkyl group and an aryl group and which is not cyclized, or a nitrogen-containing $C_{1-30}$, preferably $C_{1-20}$, five-membered to eight-membered, preferably five-membered heterocyclic ring which is bonded to the residue through a nitrogen atom which may be fused with, for example, a benzene ring; $R_2$ represents a hydrogen atom, a halogen atom, an alkoxy group, an aryloxy group, an alkyl group or a dialkylamino group; $R_3$ represents a substituent group capable of bonding to the benzene ring; X represents a hydrogen atom or a group which can be eliminated by the coupling reaction with the oxidant of an aromatic primary amino developing agent (hereinafter referred to as an eliminable group); and L represents an integer of 0 to 4, and when L is 2 or greater, the two or more $R_3$ groups may be the same or different.

In the following description of $R_3$ and X when $R_3$ represents a group containing a carbon atom, the total carbon number is from 1 to 50, preferably from 1 to 36, and when X represents a group containing a carbon atom, the total carbon number is from 1 to 30, preferably from 1 to 20.

Examples of $R_3$ include a halogen atom, an alkyl group, an aryl group, an alkoxy group, an alkoxycarbonyl group, an aryloxycarbonyl group, a carbonamido group, a sulfonamido group, a carbamoyl group, a sulfamoyl group, an alkylsulfonyl group, an arylsulfonyl group, a ureido group, a sulfamoylamino group, an alkoxycarbonylamino group, nitro group, a heterocyclic group, cyano group, an acyl group, an acyloxy group, an alkylsulfonyloxy group and an arylsulfonyloxy group. Examples of the eliminable group represented by X include a heterocyclic group attached to the coupling active site through a nitrogen atom, an aryloxy group, an arylthio group, an acyloxy group, an alkylsulfonyloxy group, a heterocyclic oxy group and a halogen atom.

In formula (Y), $R_1$ is preferably a t-butyl group, a phenyl group, a 1-alkylcyclopropyl group which may be substituted (e.g., cyclopropylmethyl, cyclopropylethyl), an indolinyl group which may be substituted (e.g., indolinyl), a 1-pyrrolidinyl group which may be substituted or a halogen-, a $C_{1-18}$ alkyl group- or a $C_{1-18}$ alkoxy group-substituted phenyl group; $R_2$ is preferably a halogen atom, a trifluoromethyl group, a $C_{1-24}$ alkoxy group or a $C_{6-24}$ phenoxy group; $R_3$ is preferably a halogen atom, a $C_{1-30}$ alkoxy group, a $C_{1-30}$ alkoxycarbonyl group, a $C_{1-30}$ carbonamido group, a $C_{1-30}$ sulfonamido group, a $C_{1-30}$ carbamoyl group or a $C_{1-30}$ sulfamoyl group; X is preferably a $C_{6-18}$ aryloxy group or a five-membered to seven-membered heterocyclic ring attached to the coupling active site through a nitrogen atom, said heterocyclic ring has 2 to 24 carbon atoms and the hetero ring may comprise any of N, S, O and P as the hetero atom; and L is preferably an integer of 0 to 2.

In formula (Y), the effects of the present invention are pronounced when $R_1$ is a t-butyl group, a cyclopropylmethyl group, a cyclopropylethyl group or an indolinyl group. Most preferred is a cyclopropylethyl group or an indolinyl group.

In formula (Y), the effects of the present invention are pronounced when $R_2$ is a halogen atom or an alkoxy group particularly preferred is a $C_{1-18}$ alkoxy group.

The couplers represented by formula (Y) may be in the form of a dimer or a polymer where two or more coupler units are bonded to each other through a bivalent or polyvalent group at the position of X, $R_2$ or $R_3$, or in the form of a homopolymer or a copolymer containing a non-color forming polymer unit.

Non-limiting examples of the coupler represented by formula (Y) include the following compounds.

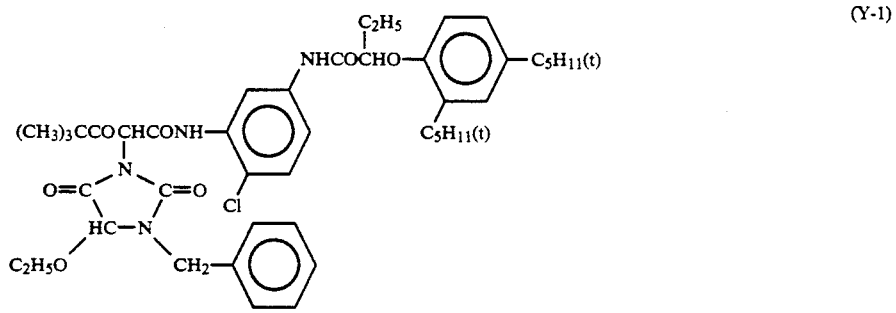

(Y-1)

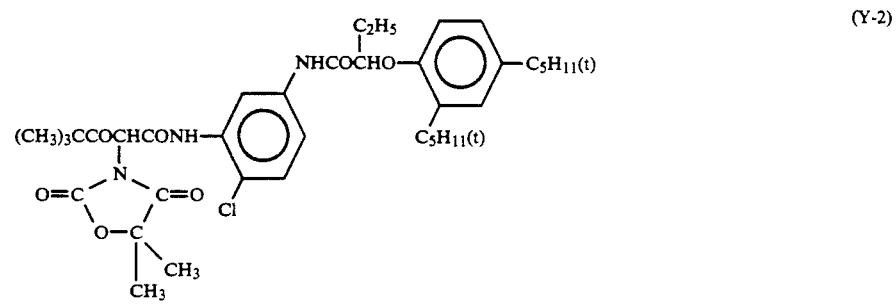

(Y-2)

-continued
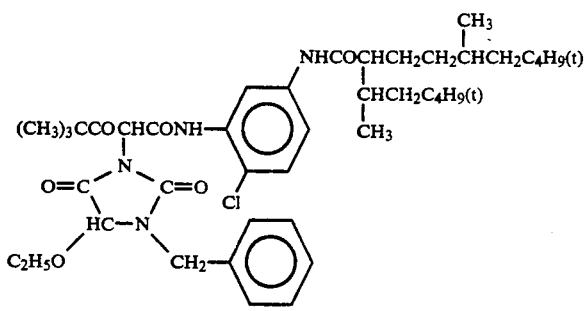
(Y-3)
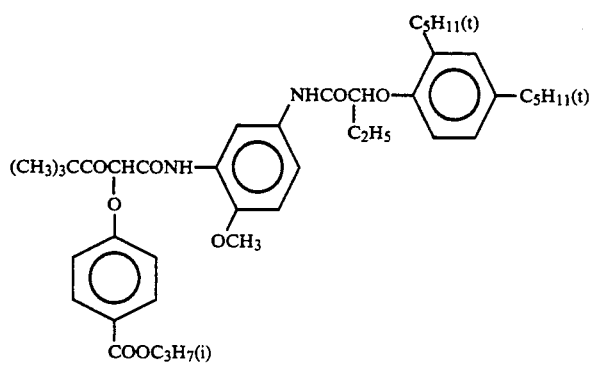
(Y-4)
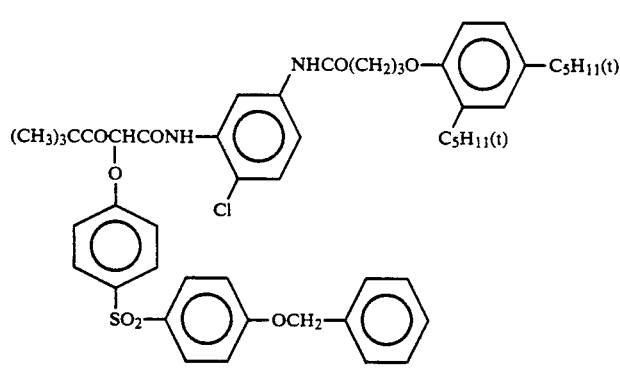
(Y-5)
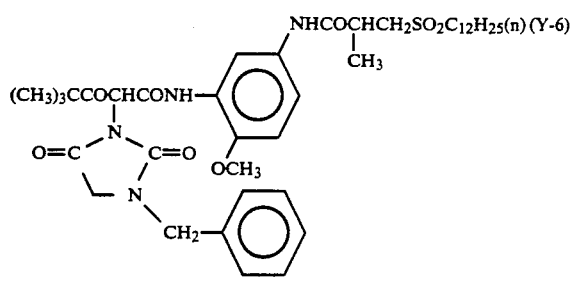
(Y-6)
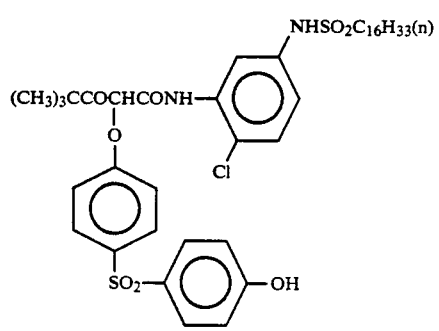
(Y-7)

-continued
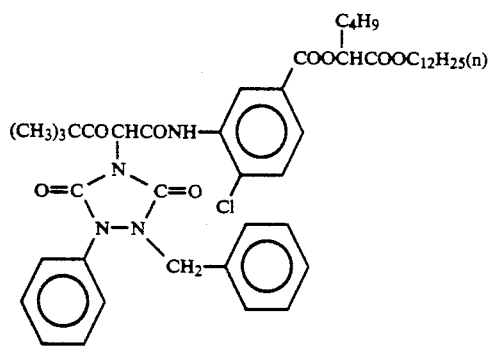
(Y-8)
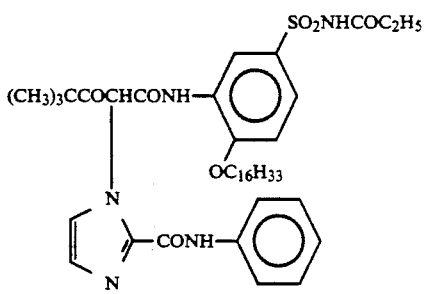
(Y-9)
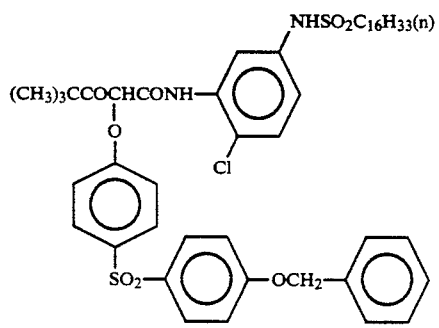
(Y-10)
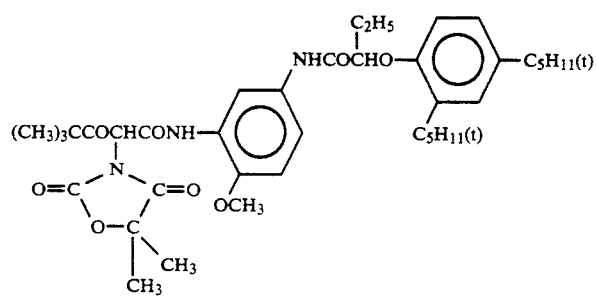
(Y-11)
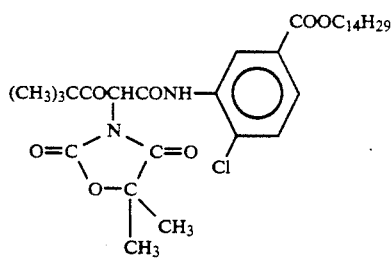
(Y-12)
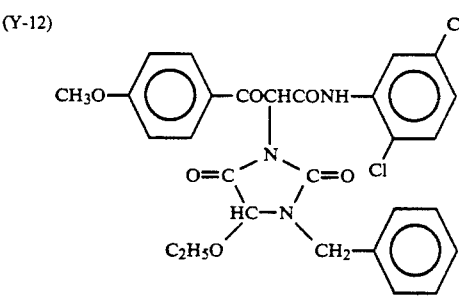
(Y-13)
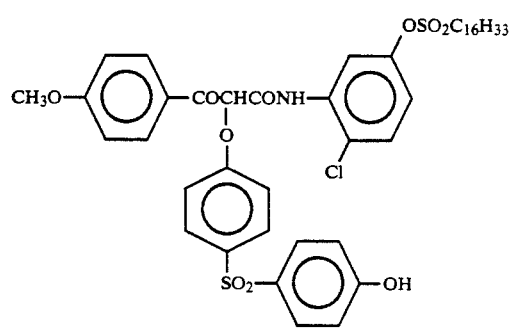
(Y-14)

-continued
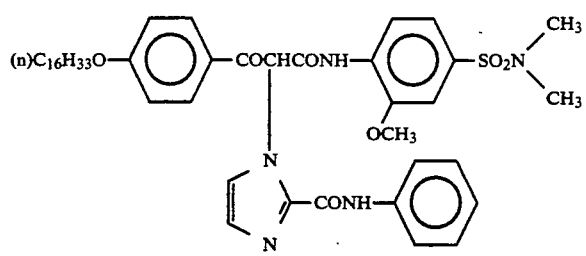 (Y-15)
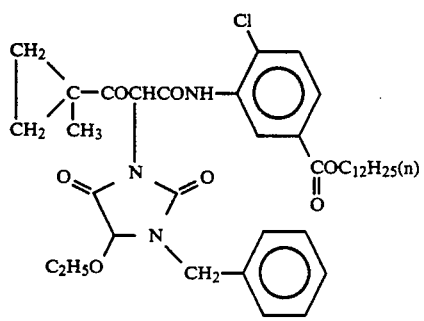 (Y-16)
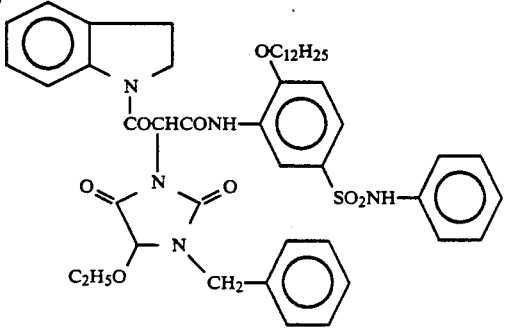 (Y-17)
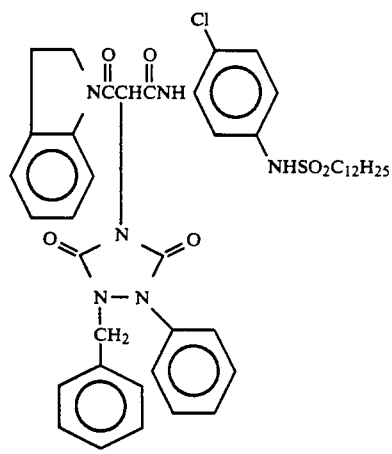 (Y-18)
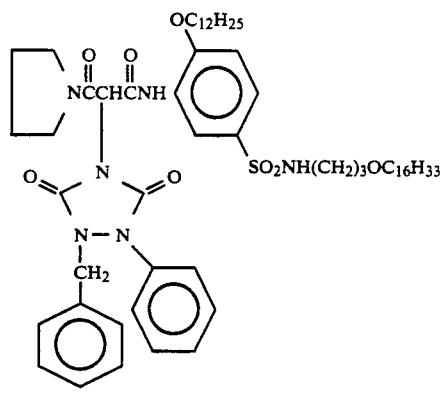 (Y-19)
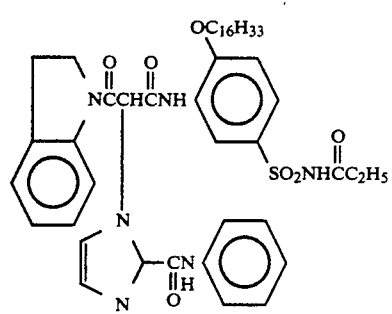 (Y-20)
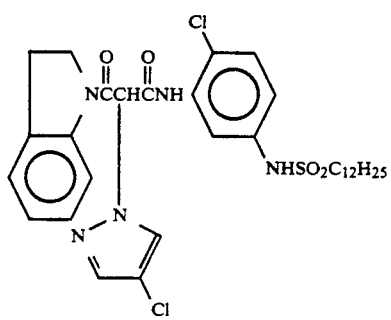 (Y-21)

-continued
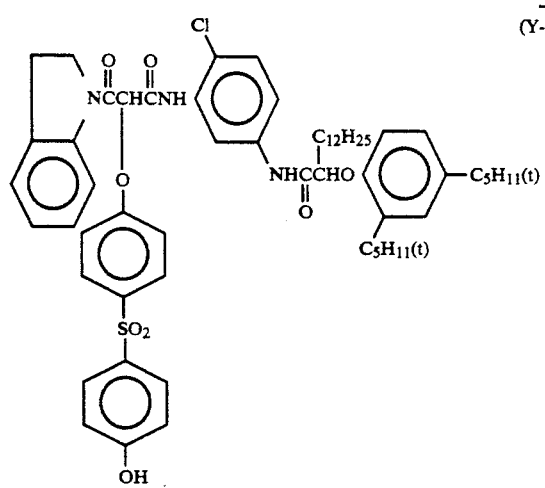
(Y-22)
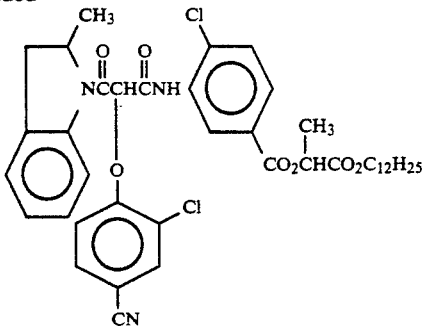
(Y-23)
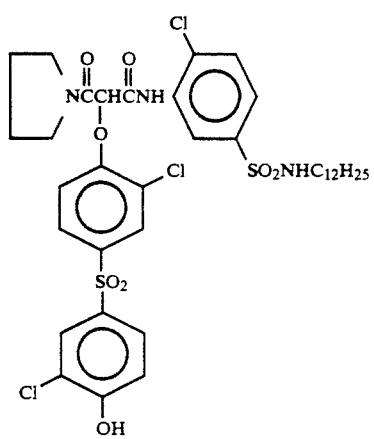
(Y-24)
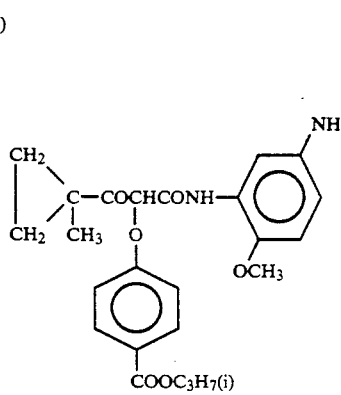
(Y-25)
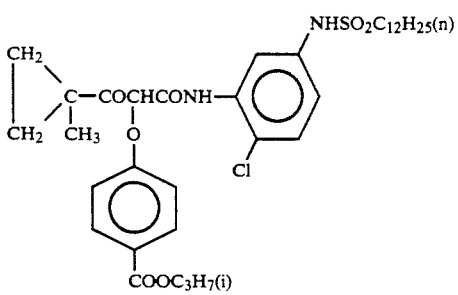
(Y-26)
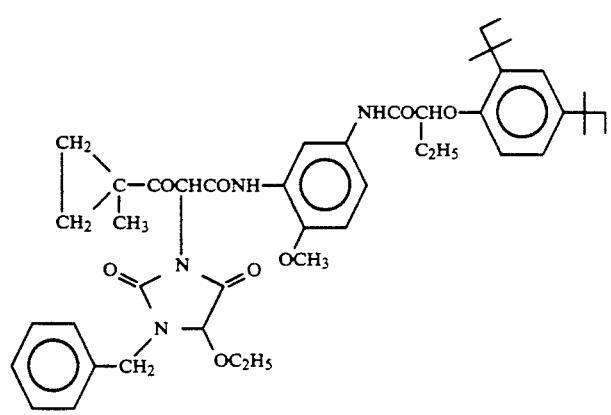
(Y-27)
Examples of other yellow couplers for use in the present invention in combination with the compound represented by formula (I) and/or examples of methods for synthesizing these yellow couplers are described in, for example, U.S. Pat. Nos. 3,227,554, 3,408,194, 3,894,875, 3,933,501, 3,973,968, 4,022,620, 4,057,432, 4,115,121, 4,203,768, 4,266,019, 4,314,023, 4,327,175, 4,401,752, 4,404,274, 4,420,556, 4,711,837 and 4,729,944, European Patents 30,747A, 296,793A and 313,308A, West German Patent 3,107,173C, JP-A-59-174839, and JP-A-63-123047. The methods for synthesizing the dimer couplers are described, for example, in U.S. Pat. No. 4,248,961 and those for the polymeric couplers in, for example, European Patent 248,081A, JP-A-58-42044 and JP-A-62-276547.

The yellow coupler is generally used in an amount of 0.001 to 1 mol, preferably 0.01 to 0.5 mol per mol of light-sensitive silver halide contained in the same layer.

Cyan couplers for use in the present invention in combination with the compound represented by formula (I) in the same layer may be any cyan couplers and examples are described in U.S. Pat. Nos. 2,369,929, 4,511,647, 2,772,162, 4,500,653 and 4,564,586, European Patent Laid-Open No. EP0,249,453A2, JP-A-61-390441, JP-A-61-153640, JP-A-62-257158 and Japanese Patent Application Nos. 2-334786 and 2-326218.

Cyan couplers preferably used in the same layer with the compound of formula (I) according to the present invention are compounds represented by the following formula (C-I) or (C-II).

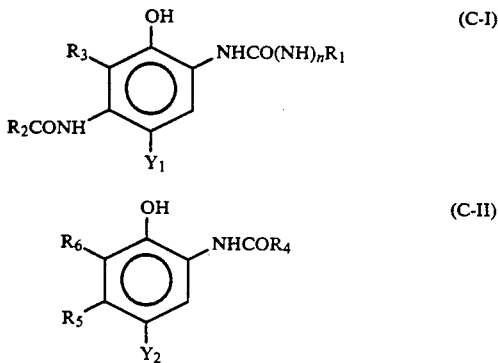

In formulae (C-I) and (C-II), $R_1$, $R_2$ and $R_4$ each represents a $C_{1-50}$, preferably $C_{1-36}$ aliphatic group, a $C_{6-56}$, preferably $C_{6-36}$ aromatic group or a $C_{1-50}$, preferably $C_{1-36}$ heterocyclic group of five-membered to eight-membered ring comprising any of O, S, N and P as the hetero atom; $R_3$, $R_5$ and $R_6$ each represents a hydrogen atom, a halogen atom, a $C_{1-50}$, preferably $C_{1-36}$ aliphatic group, a $C_{6-56}$, preferably $C_{6-36}$ aromatic group or a $C_{2-50}$, preferably $C_{2-36}$ acylamino group, or $R_3$ is a nonmetallic atomic group for forming a nitrogen-containing five-membered or six-membered heterocyclic ring together with $R_2$; $Y_1$ and $Y_2$ each represents a hydrogen atom or a group which is eliminated by the coupling reaction with the oxidant of an aromatic primary amino developing agent; and n represents 0 or 1.

Examples of heterocyclic groups represented by $R_1$, $R_2$ or $R_4$ include 2-pyridyl, 4-pyridyl, 2-furyl, 4-thienyl, 2-piperidyl, 1-imidazolyl, 1-pyrazolyl, 1,2,4-triazole-1-yl, 1,2,3,4-tetrazole-1-yl, 1,2,3,4-tetrazole-2-yl, benzimidazole-1-yl, 1,2,3-triazole-1-yl and benzotriazole-2-yl. Examples of heterocyclic rings formed by $R_2$ and $R_3$ include carbostyril.

In formula (C-II), $R_5$ is preferably an aliphatic group such as methyl group, ethyl group, propyl group, butyl group, pentadecyl group, t-butyl group, cyclohexyl group, cyclohexylmethyl group, phenylthiomethyl group, dodecyloxyphenylthiomethyl group, butaneamidomethyl group or methoxymethyl group.

Among the cyan couplers of formulae (I) and (II), the following compounds are preferred.

In formula (C-I), $R_1$ is preferably an aryl group or a heterocyclic group. More preferred is an aryl group substituted by a halogen atom, an alkyl group, an alkoxy group, an aryloxy group, an acylamino group, an acyl group, a carbamoyl group, a sulfonamido group, a sulfamoyl group, a sulfonyl group, a sulfamido group, oxycarbonyl group or cyano group.

When $R_3$ does not form a ring together with $R_2$ in formula (C-I), $R_2$ is preferably an alkyl group or an aryl group. Particularly preferred is an aryloxy-substituted alkyl group. $R_3$ is preferably a hydrogen atom.

In formula (C-II), $R_4$ is preferably an alkyl group or an aryl group. Particularly preferred is an aryloxy-substituted alkyl group.

In formula (C-II), $R_5$ is preferably an alkyl group having 2 to 15 carbon atoms or a methyl group having a substituent group having one or more carbon atoms. Preferred examples of the substituent group include an arylthio group, an acylamino group, an aryloxy group and an alkyloxy group.

In formula (C-II), $R_5$ is more preferably an alkyl group having 2 to 15 carbon atoms, particularly preferably 2 to 4 carbon atoms.

In formula (C-II), $R_6$ is preferably hydrogen atom or a halogen atom with chlorine atom or fluorine atom being particularly preferred. In formulae (C-I) and (C-II), $Y_1$ and $Y_2$ each preferably represents a hydrogen atom, a halogen atom, a $C_{1-50}$, preferably $C_{1-36}$ alkoxy group, a $C_{6-56}$, preferably $C_{6-36}$ aryloxy group, a $C_{2-50}$, preferably $C_{2-36}$ acyloxy group or a $C_{1-50}$, preferably $C_{1-36}$ sulfonamido group.

The compounds of the present invention may be used in combination with the azole cyan couplers typified by compounds described in, for example, European Patent Laid-Open No. EP0,249,453A2.

Non-limiting examples of the cyan couplers of formulae (C-I) and (C-II) include the following compounds.

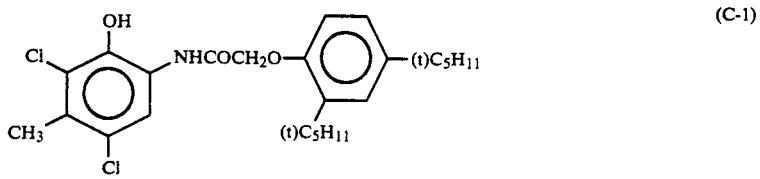

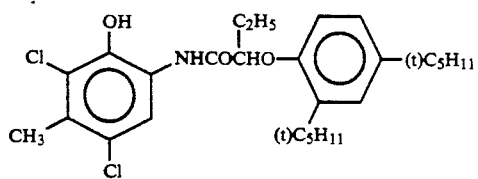 (C-2)
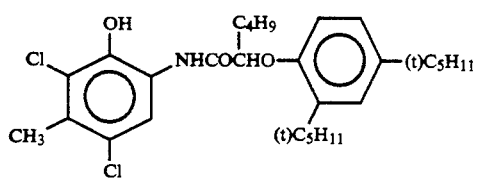 (C-3)
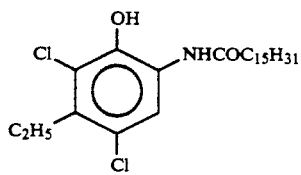 (C-4)
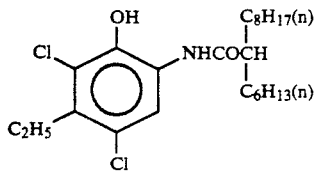 (C-5)
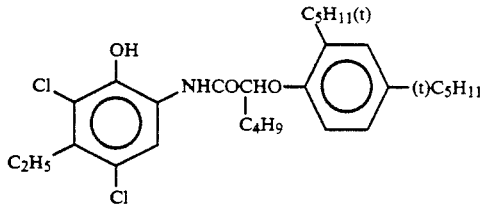 (C-6)
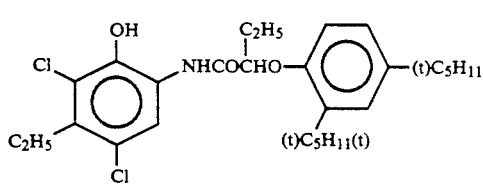 (C-7)
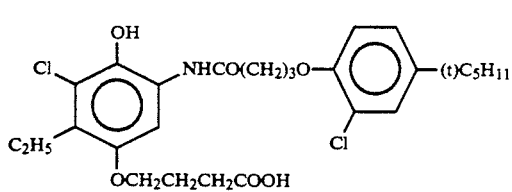 (C-8)
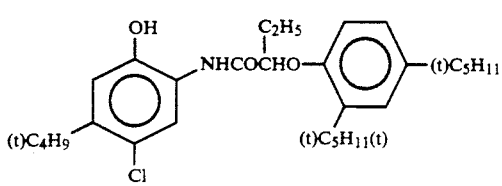 (C-9)

-continued
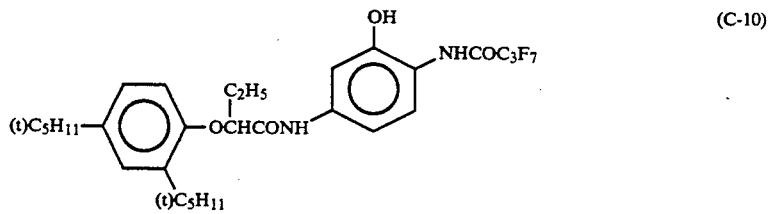 (C-10)
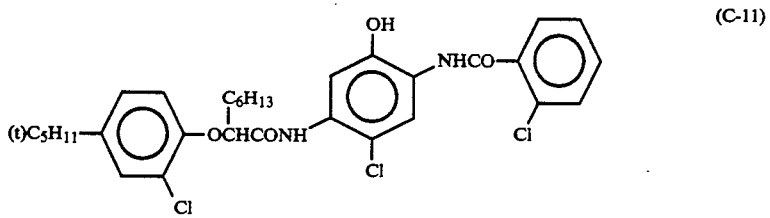 (C-11)
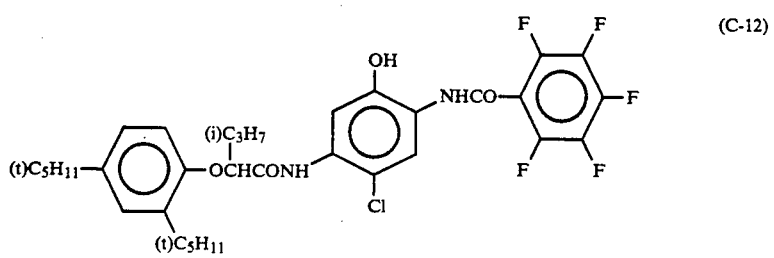 (C-12)
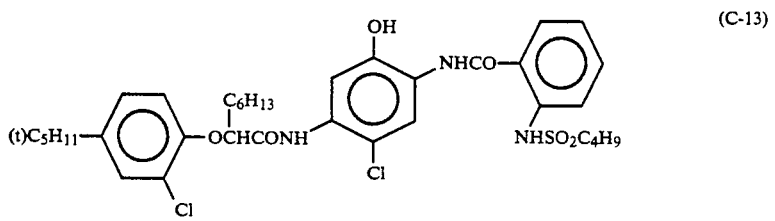 (C-13)
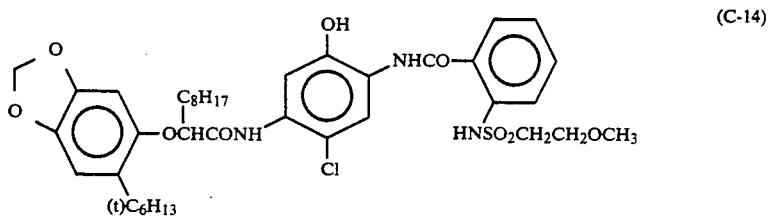 (C-14)
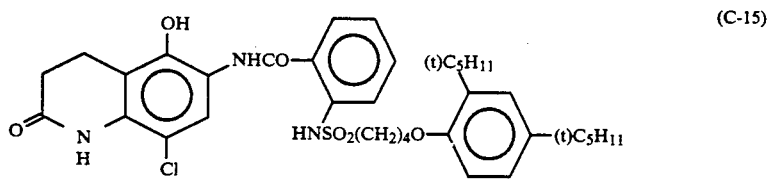 (C-15)
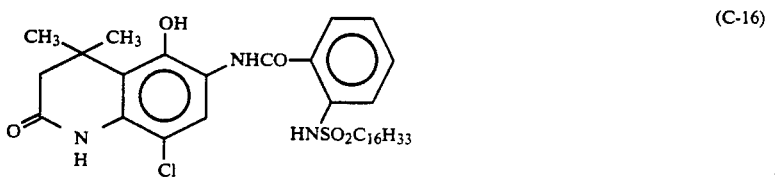 (C-16)

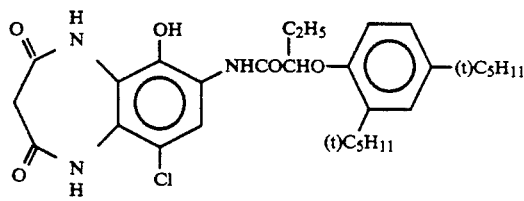
(C-17)
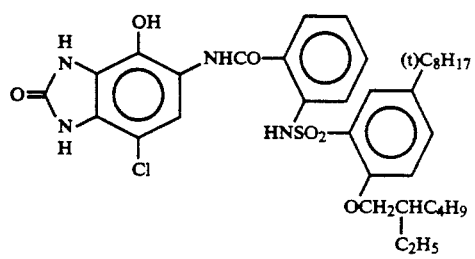
(C-18)
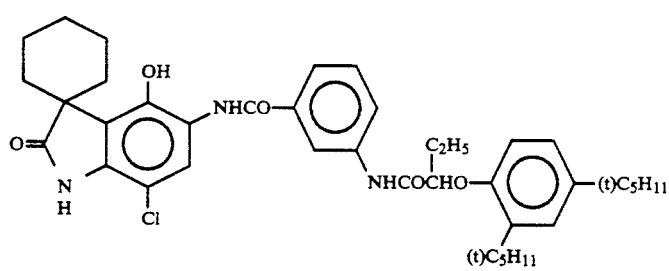
(C-19)
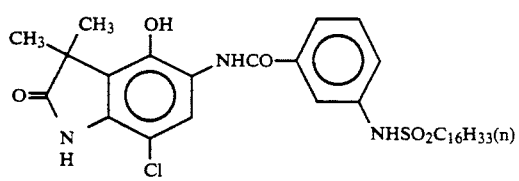
(C-20)
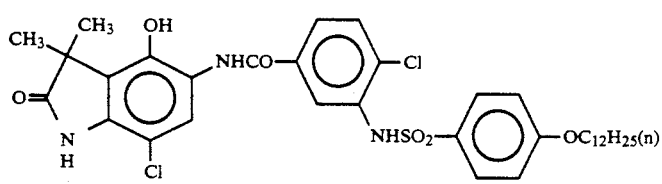
(C-21)
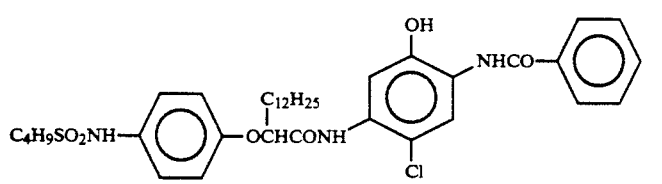
(C-22)
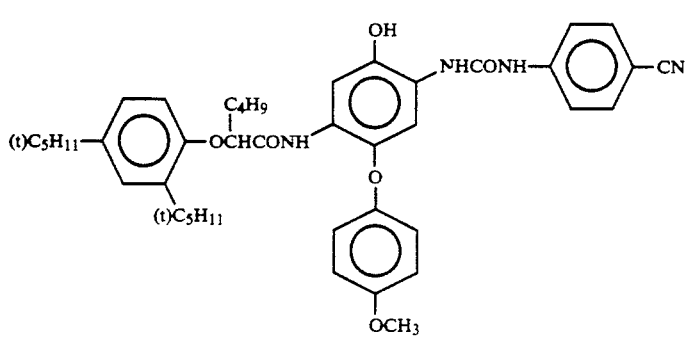
(C-23)

(C-24)

The above described cyan couplers can be synthesized according to the methods described in U.S. Pat. Nos. 2,369,929, 4,511,647, 2,772,162, 4,500,653 and 4,564,586, European Patent Laid-Open No. EP0,249,4-53A2, JP-A-61-390441, JP-A-61-153640 and JP-A-62-257158.

The cyan coupler is generally used in an amount of 0.001 to 1 mol, preferably 0.002 to 0.3 mol per mol of light-sensitive silver halide contained in the same layer.

The compounds of formula (I) of the present invention are illustrated below.

The substituent groups $R_{21}$, $R_{22}$, $R_{23}$, $R_{24}$, $R_{25}$, $R_{26}$, $R_{27}$, $R_{28}$, $R_{29}$, $R_{32}$, $R_{33}$ and $R_{34}$ of formula (I) are illustrated in detail below.

The halogen atom includes fluorine atom, chlorine atom and bromine atom. The aromatic group is a $C_{6-46}$, preferably $C_{6-36}$ group and examples thereof include phenyl group, 4-methoxyphenyl group and 2-hydroxyphenyl group.

The aliphatic oxy group is a $C_{1-40}$, preferably $C_{1-30}$ group and examples thereof include methoxy group, octyloxy group, i-propyloxy group, Sec-butyloxy group, dodecyloxy group, benzyloxy group, allyloxy group and cyclohexyloxy group.

The aromatic oxy group is a $C_{6-46}$, preferably $C_{6-36}$ group and examples thereof include phenoxy group, 4-methoxyphenoxy group and 4-dodecyloxyphenoxy group.

The aliphatic thio group is a $C_{1-40}$, preferably $C_{1-30}$ group and examples thereof include methylthio group, t-butylthio group and dodecylthio group. The aromatic thio group is a $C_{6-46}$, preferably $C_{6-36}$ group and examples thereof include phenylthio group and 2-t-butyl-thio group.

The aliphatic and aromatic acyl groups are $C_{1-46}$, preferably $C_{1-36}$ groups and examples thereof include acetyl group, pivaloyl group, i-butyryl group, myristyl group, acryloyl group, benzoyl group and p-methoxy benzoyl group.

The aliphatic oxycarbonyl group is a $C_{2-42}$, preferably $C_{2-32}$ group and examples thereof include methoxycarbonyl group and dodecylcarbonyl group. The aromatic oxycarbonyl group is a $C_{7-47}$, preferably $C_{7-37}$ group and examples thereof include phenoxycarbonyl group and 4-t-butylphenoxycarbonyl group.

The aliphatic acylamino group is a $C_{2-42}$, preferably $C_{2-32}$ group and the aromatic acylamino group is a $C_{7-47}$, preferably $C_{7-37}$ group and examples of these groups include acetylamino group, myristoylamino group, N-methylacetylamino group, methacryloylamino group, 4-t-butylphenoxyacetylamino group and benzoylamino group. The aliphatic sulfonamido group is a $C_{2-42}$, preferably $C_{2-32}$ group and examples thereof include N-methylmethanesulfonamido group and octanesulfonamido group. The aromatic sulfonamido group is a $C_{6-46}$, preferably $C_{6-36}$ group and examples thereof include benzenesulfonamido group and p-methoxybenzenesulfonamido group.

The imido group is a $C_{2-42}$, preferably $C_{2-32}$ group and examples thereof include succinimido group and dodecylsuccinimido group. The aliphatic and aromatic acyloxy groups are $C_{2-47}$, preferably $C_{2-37}$ group and examples thereof include acetyloxy group, myristoyloxy group and benzoyloxy group. The aliphatic sulfonyl group is a $C_{1-40}$, preferably $C_{1-30}$ group and examples thereof include methanesulfonyl group and hexadecylsulfonyl group.

The aromatic sulfonyl group is a $C_{6-46}$, preferably $C_{6-36}$ group and examples thereof include benzenesulfonyl group and p-dodecyloxybenzenesulfonyl group. The aliphatic sulfonyloxy group is a $C_{1-40}$, preferably $C_{1-30}$ group and examples thereof include methanesulfonyloxy group and dodecylsulfonyloxy group. The aromatic sulfonyloxy group is a $C_{6-46}$, preferably $C_{6-36}$ group and examples thereof include benzenesulfonyloxy group and p-methoxybenzenesulfonyloxy group.

The aliphatic oxycarbonylamino group is a $C_{2-40}$, preferably $C_{2-30}$ group and examples thereof include methoxycarbonylamino group and N-methyloctyloxycarbonylamino group. The aromatic oxycarbonylamino group is a $C_{7-47}$, preferably $C_{7-37}$ group and examples thereof include phenoxycarbonylamino group and 2,4-di-t-butylphenoxycarbonylamino group. The carbamoylamino group is a $C_{1-40}$, preferably $C_{1-30}$ group and examples thereof include N,N-dimethylcarbamoylamino group and N-octylcarbamoylamino group. The sulfamoylamino group is a $C_{0-40}$, preferably $C_{0-30}$, group and examples thereof include N,N-diethylsulfamoylamino group and N-octyl-N-methylsulfamoylamino group.

The carbamoyl group is a $C_{1-40}$, preferably $C_{1-30}$ group and examples thereof include N,N-diethylcarbamoyl group, N-octylcarbamoyl group and N-phenylcarbamoyl group. The sulfamoyl group is a $C_{0-40}$, preferably $C_{0-30}$ group and examples thereof include N,N-dimethylsulfamoyl group and N-phenylsulfamoyl group.

The heterocyclic group is a $C_{1-40}$, preferably $C_{1-30}$, five-membered to seven-membered group containing O, N, S or P as the hetero atom and examples thereof include 2-pyridyl group and 1-piperidyl group. The aliphatic group is a $C_{1-40}$, preferably $C_{1-30}$ group and examples thereof include methyl group, i-butyl group, t-butyl group, t-octyl group, dodecyl group, 2-ethylhexyl group, allyl group, methoxyethyl group, benzyl group, cyclohexyl group and phenethyl group.

Among the compounds of formula (I) of the present invention, the compounds represented by the following formula (I-A) are preferred for providing the effects of the present invention.

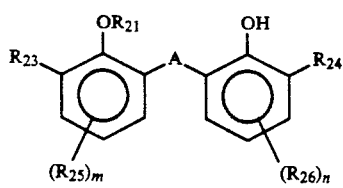

(I-A)

In formula (I-A), $R_{21}$, $R_{23}$, $R_{24}$, $R_{25}$, $R_{26}$, A, m and n are as defined above in formula (I).

Among the compounds of formula (I-A) according to the present invention, the compounds represented by the following general formula (I-B) are more preferred for providing the effects of the present invention.

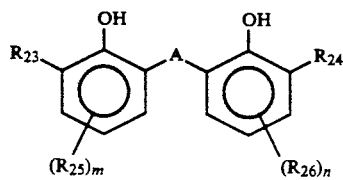

(I-B)

In formula (I-B), $R_{23}$, $R_{24}$, $R_{25}$, $R_{26}$, A, m and n are as defined above in formula (I).

Among the compounds represented by formulae (I), (I-A) and (I-B) of the present invention, the compounds where A is —C($R_{28}$)($R_{29}$)— or —O— are preferred for providing the effects of the present invention. Compounds where one of $R_{28}$ and $R_{29}$ in the group —C($R_{28}$)($R_{29}$)— is a hydrogen atom and the other is an aliphatic group are more preferred. The aliphatic group is preferably an alkyl group, with an alkyl group having 1 to 12 carbon atoms being more preferred.

Among the compounds of formula (I), (I-A) and (I-B) according to the present invention, compounds where $R_{23}$ and $R_{24}$ are each an aliphatic acylamino group, an aromatic acylamino group, an aliphatic carbamoylamino group, an aromatic carbamoylamino group, an aliphatic sulfamoylamino group, an aromatic sulfamoylamino group, an aliphatic oxy group, an imido group, an aliphatic oxycarbonylamino group or an N-alkylated aliphatic or aromatic sulfonamido group, are preferred for providing the effects of the present invention. The aliphatic portion is preferably an alkyl having 1 to 20 carbon atoms. The aromatic portion is preferably phenyl or a substituted phenyl group having 6 to 26 carbon atoms. Most preferably, $R_{23}$ and $R_{24}$ are each an alkylacylamino group, an alkylcarbamoylamino group or an alkoxycarbonylamino group.

Among the compounds of formulae (I), (I-A) and (I-B) of the present invention, compounds where $R_{25}$ and $R_{26}$ are each an aliphatic group are preferred for providing the effects of the present invention. More preferred is a straight-chain alkyl group.

The compounds of formula (I) of the present invention may be used in combination with conventional anti-fading agents (fading inhibitors), to further increase the fade inhibiting effect. The compounds of formula (I) may be used either alone or in combination of two or more thereof.

The addition amount of the compound of formula (I) varies depending on the nature and type(s) of the couplers to be used, but is generally in the range of 0.5 to 300 mol%, preferably 1 to 200 mol% based on the amount of the coupler contained in the same layer.

Typical examples of the compounds of formula (I) include, but are not limited to, the following compounds.

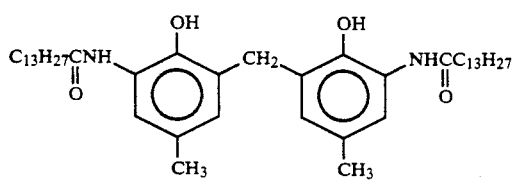

(I-1)

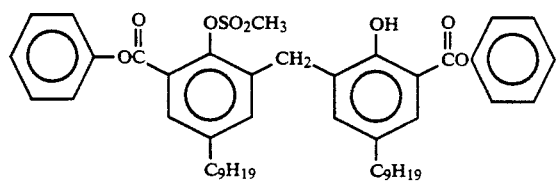

(I-2)

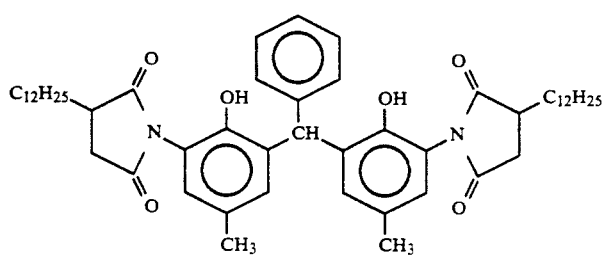

(I-3)

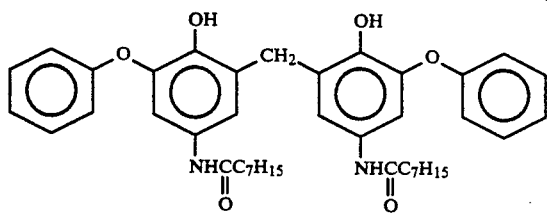
(I-4)
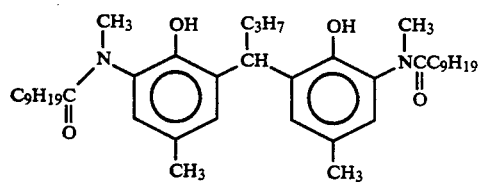
(I-5)
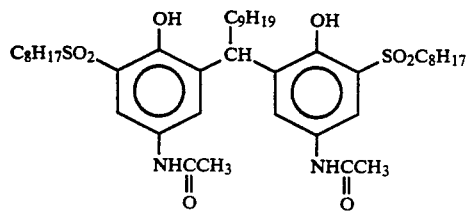
(I-6)
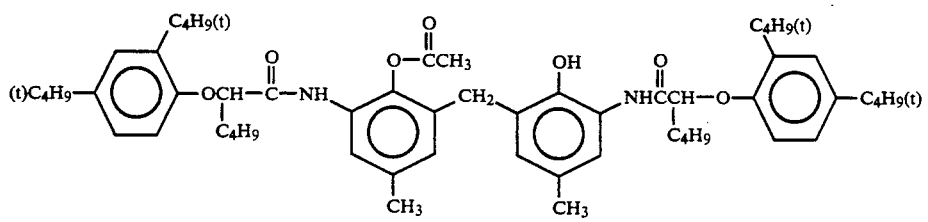
(I-7)
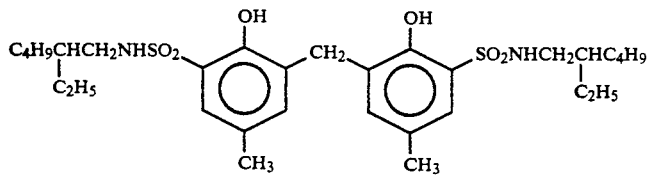
(I-8)
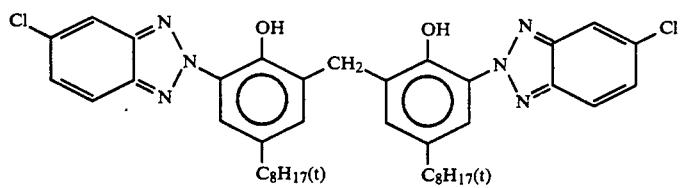
(I-9)
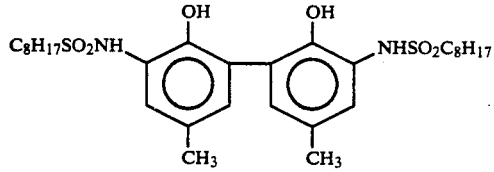
(I-10)
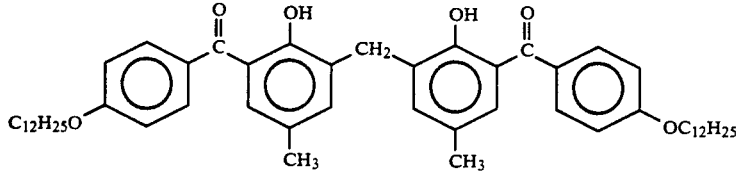
(I-11)

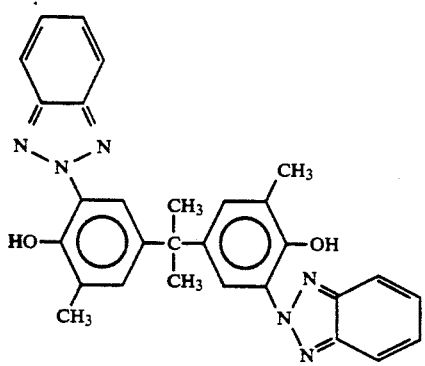
(I-12)
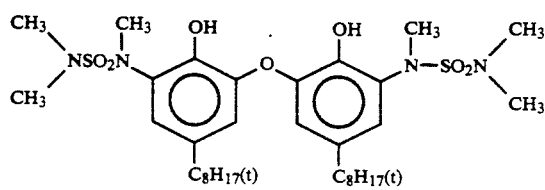
(I-13)
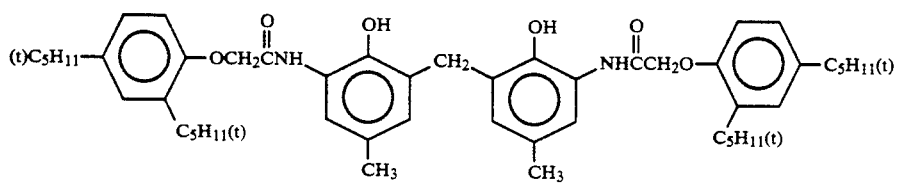
(I-14)
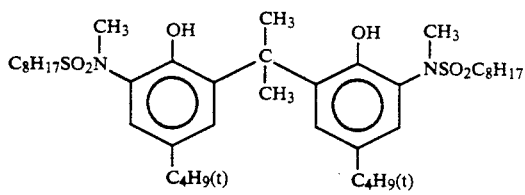
(I-15)
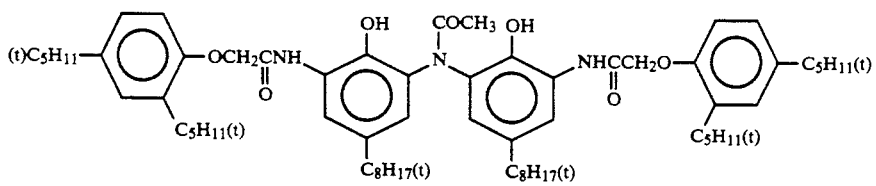
(I-16)
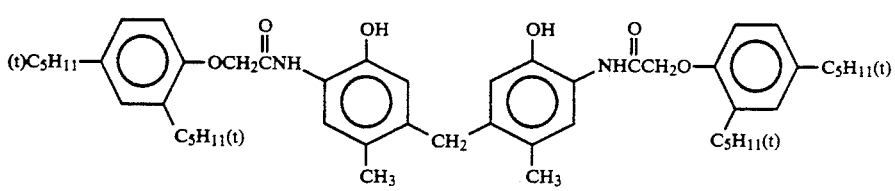
(I-17)
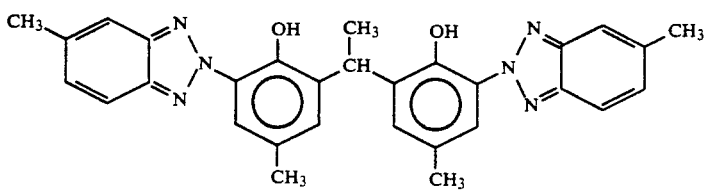
(I-18)

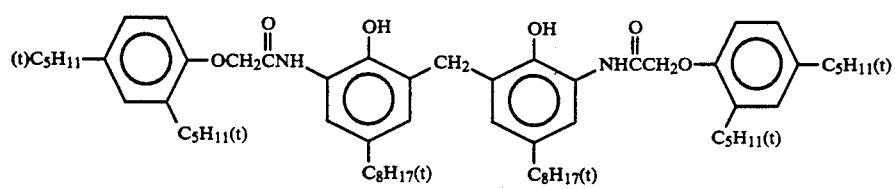
(I-19)
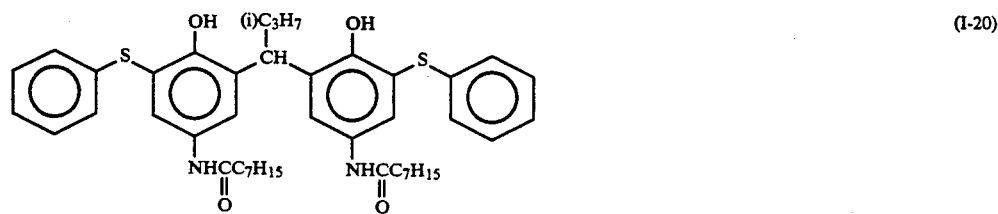
(I-20)
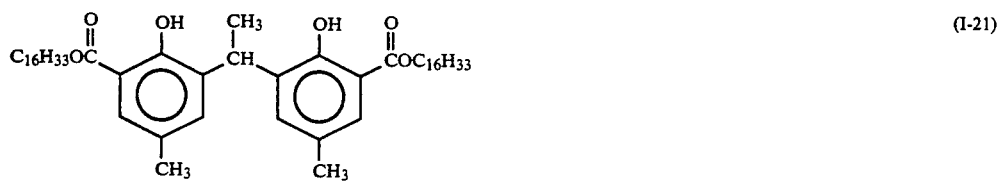
(I-21)
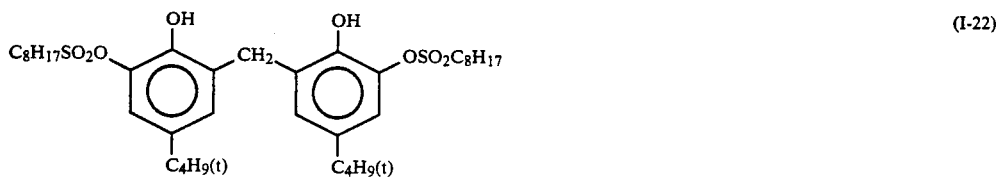
(I-22)
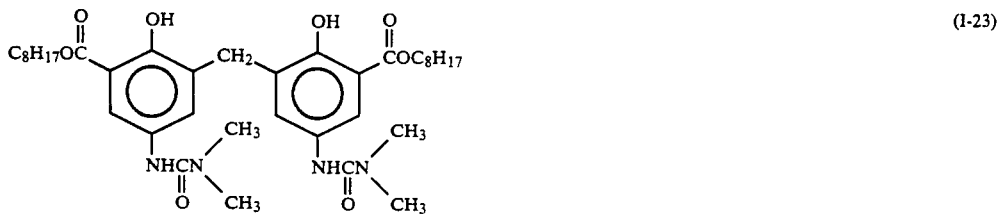
(I-23)
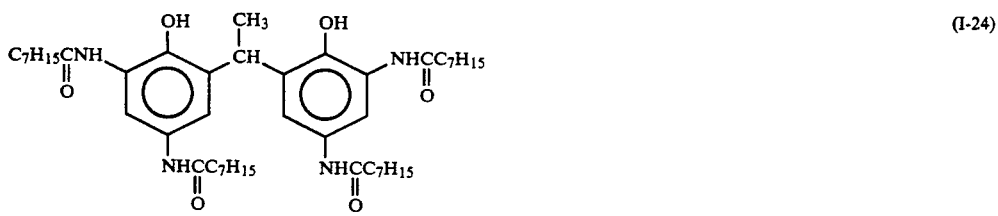
(I-24)
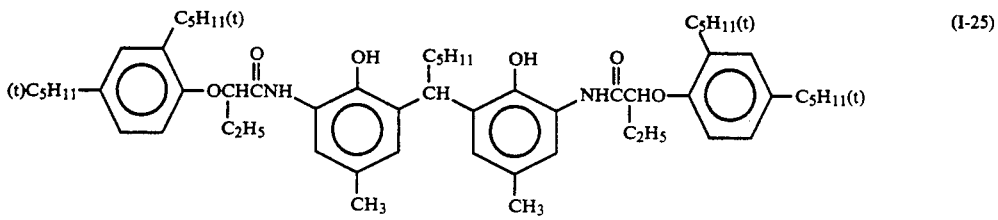
(I-25)

-continued
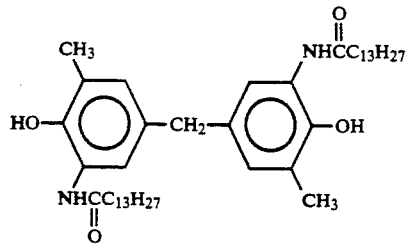 (I-26)
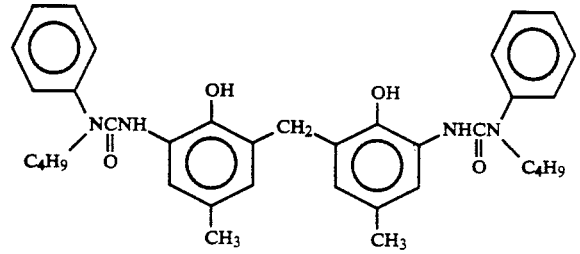 (I-27)
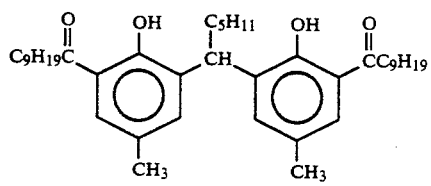 (I-28)
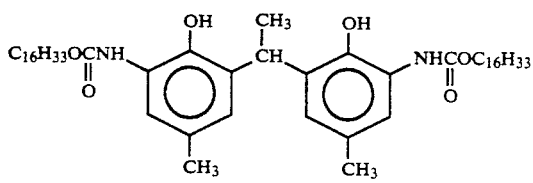 (I-29)
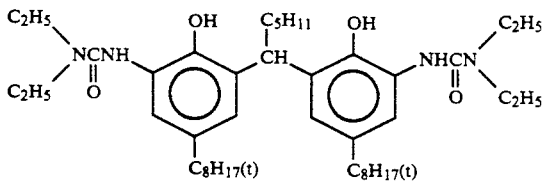 (I-30)
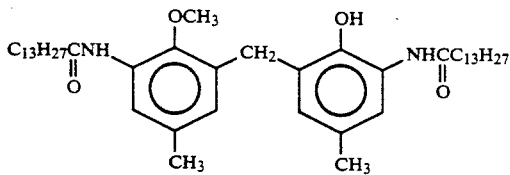 (I-31)
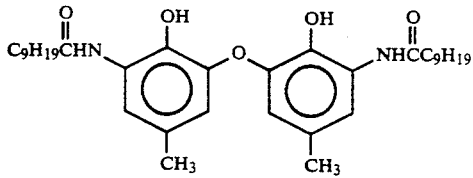 (I-32)
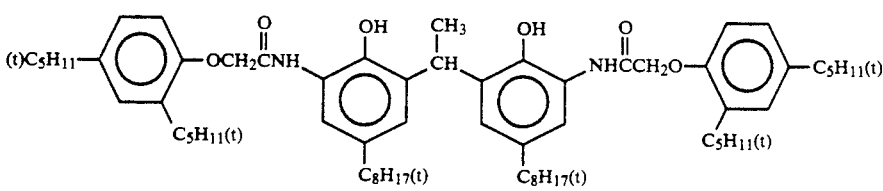 (I-33)

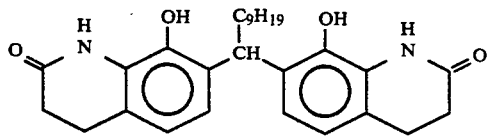
(I-34)
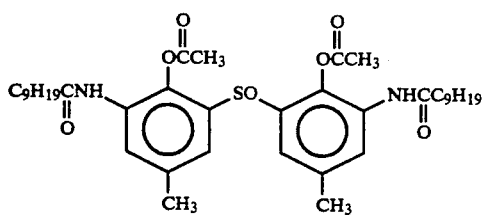
(I-35)
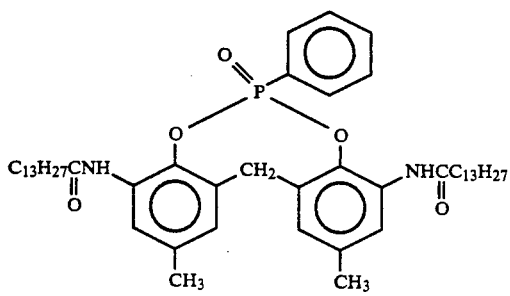
(I-36)
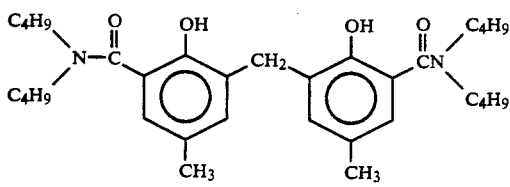
(I-37)
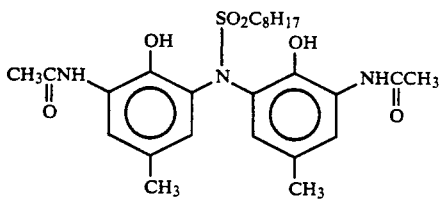
(I-38)
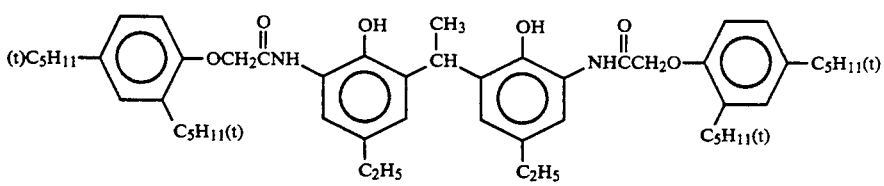
(I-39)
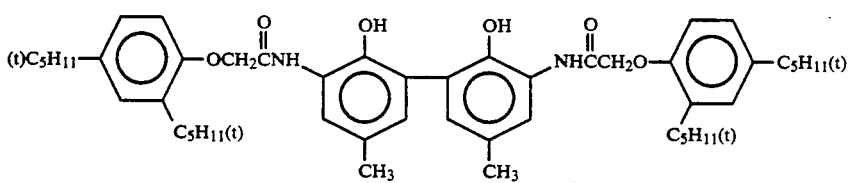
(I-40)
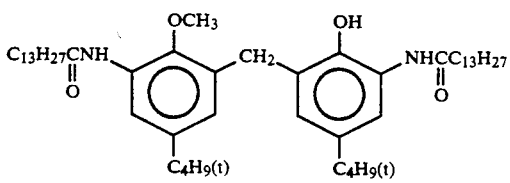
(I-41)

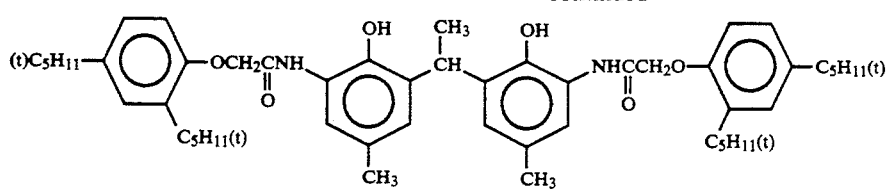
(I-42)
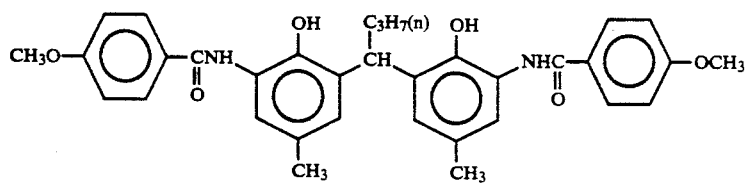
(I-43)
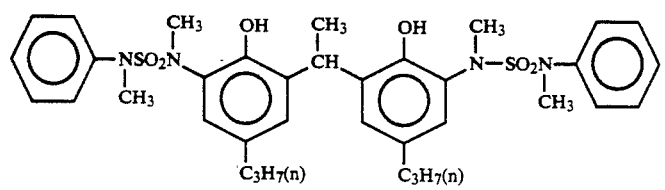
(I-44)
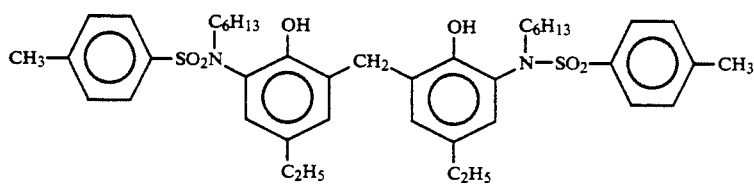
(I-45)
The compounds of formula (I) of the present invention can be synthesized according to the methods described in JP-A-50-6338, JP-A-50-87326, *J. Am. Chem. Soc.*, Vol. 75, page 947 (1953) and *J. Chem. Soc.*, page 243 (1954).
A synthesis method of a typical compound represented by formula (I) is illustrated below.
Synthesis of Compound I-42
Compound I-42 was synthesized according to the following synthesis route.
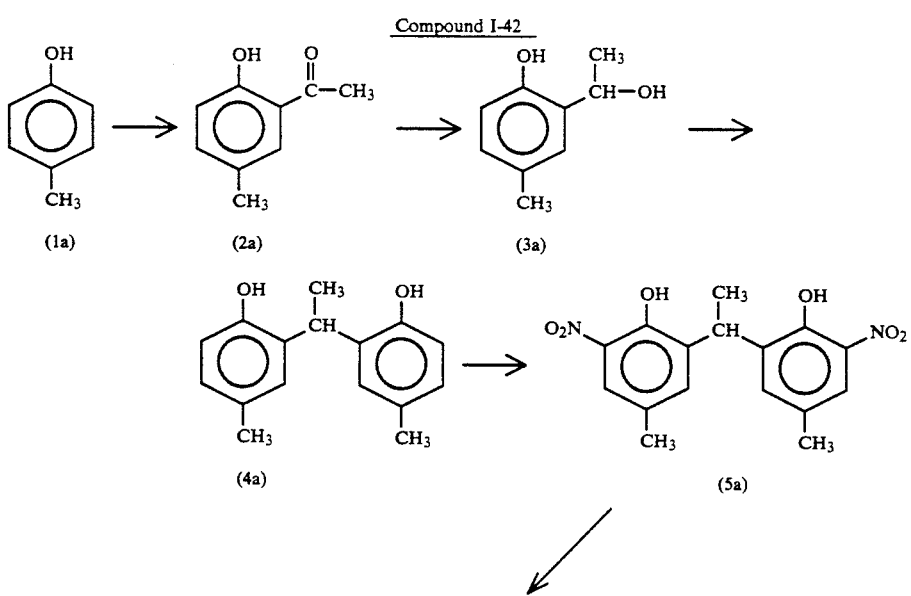

Compound I-42

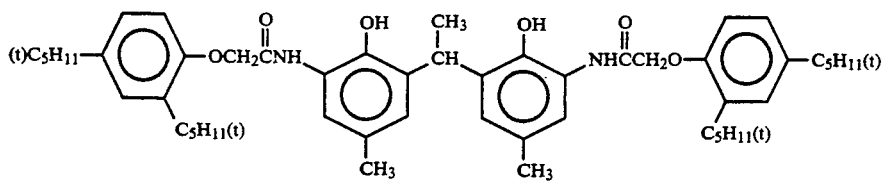

To 60 g of p-cresol (1a), there were added 50 ml of chlorobenzene. Subsequently, 44 ml of acetyl chloride were added dropwise therto over a period of 30 minutes while heating the mixture on a seam bath with stirring. The mixture was heated with stirring for an additional two hours, and 75 g of anhydrous aluminum chloride was added therto over a period of 30 minutes. The mixture was then heated with stirring for 2 hours. The reaction mixture (solution) was added to 300 ml of ice water, and extracted with 300 ml of ethyl acetate. The ethyl acetate layer was washed twice with 300 ml of brine. Ethyl acetate was distilled off under reduced pressure, and the residue was crystallized from 400 ml of n-hexane:ethyl acetate (10:1) to obtain a light yellow crystal. NMR spectrum, MS spectrum and IR-spectrum showed that the crystal was compound (2a). Yield: 68.0 g. Melting point: 46° to 47° C.

In 200 ml of isopropyl alcohol were dissolved 50 g of compound (2a), and 24 g of sodium boron hydride was gradually added thereto at 20° to 22° C. with stirring. The reaction mixture was stirred for 5 hours, and gradually added to 200 ml of ice water containing 40 ml of acetic acid. The mixture was extracted with 500 ml of diethyl ether was conducted. The diethyl ether layer was washed with 200 ml of brine. Diethyl ether was distilled off, and the residue was crystallized from 80 ml of n-hexane. NMR spectrum, MS spectrum and IR spectrum showed that the resulting crystal was compound (3a). Yield: 32 g. Melting point: 82° to 84° C.

In 100 ml of acetic acid were dissolved 11 g of compound (3a) and 20 g of p-cresol, and 0.3 ml of concentrated sulfuric acid was slowly added thereto at 15° to 20° C. with stirring. The reaction mixture was stirred for 2 hours, and added to 100 ml of ice water. The mixture was extracted with 100 ml of ethyl acetate. The ethyl acetate layer was washed twice with 100 ml of brine. Ethyl acetate was distilled off under reduced pressure. The residue was purified by means of silica gel column chromatograph. The product was crystallized from 50 ml of n-hexane to obtain a white crystal. NMR spectrum, MS spectrum and IR spectrum showed that the crystal was compound (4a). Yield: 13.5 g. Melting point: 136° to 138° C.

In 20 ml of acetic acid were dissolved 10 g of compound (4a), and 6.5 ml of concentrated nitric acid were added dropwise thereto at 10° to 15° C. with stirring over a period of 30 minutes. The reaction mixture was stirred for one hour and added to 100 ml of ice water. The mixture was extracted with 100 ml of ethyl acetate. The ethyl acetate layer was washed twice with 100 ml of brine. Ethyl acetate was distilled off under reduced pressure. The residue was crystallized from 30 ml of n-hexane to obtain a yellow crystal. NMR spectrum, MS spectrum and IR spectrum showed that the crystal was compound (5a). Yield: 8.5 g. Melting point: 176° to 179° C.

In 50 ml of acetonitrile and 3 ml of triethylamine were dissolved 3.3 g of compound (5a), and 1.6 ml of methanesulfonyl chloride were added dropwise thereto at 5° to 10° C. with stirring. The reaction mixture was stirred for one hour and then added to 50 ml of ice water. The mixture was extracted with 100 ml of ethyl acetate. The ethyl acetate layer was washed twice with 50 ml of brine. Ethyl acetate was distilled off under reduced pressure. To the residue, there were added 100 ml of ethanol and 0.3 g of a catalyst composed of 10 wt% palladium on carbon. The mixture was stirred at 50° C. under hydrogen gas pressure (70 kg/cm$^2$) in an autoclave for 5 hours. The palladium/carbon catalyst was separated from the reaction mixture by filtration, and ethanol was distilled off under reduced pressure. The residue was dissolved in 5 ml of dimethylacetamide and 20 ml of acetonitrile, and 6.3 g of 2,4-di-t-amylphenoxyacetyl chloride were added thereto at 20° to 25° C. with stirring over a period of 10 minutes. The reaction mixture was stirred for one hour and then added to 100 ml of ice water. The mixture was extracted with 100 ml of ethyl acetate. The ethyl acetate layer was washed twice with 100 ml of brine. Ethyl acetate was distilled off under reduced pressure. The residue was added to 40 ml of a methanol solution of 5 wt% potassium hydroxide in a nitrogen gas atmosphere, and the mixture was stirred at 40° C. for 2 hours. The reaction mixture was added to 100 ml of ice water containing 3 ml of concentrated hydrochloric acid. The mixture was extracted with 100 ml of ethyl acetate. The ethyl acetate layer was washed twice with 100 ml of brine. The ethyl acetate layer was dried over anhydrous magnesium sulfate. After the magnesium sulfate was separated by filtration, ethyl acetate was distilled off under reduced pressure. The residue was crystallized from 25 ml of methanol. The resulting crystal was recrystallized from 20 ml of methanol to obtain a white crystal. NMR spectrum, MS spectrum and IR spectrum showed that the crystal was compound I-42. Yield: 4.8 g. Melting point: 163° to 165° C.

When the compound of formula (I) of the present invention is used in the same layer with a yellow coupler, the effect thereby obtained is remarkable as compared with the use of the compound of formula (I) in the same layer with a cyan coupler.

The silver halide color photographic material of the present invention generally comprises a support having thereon in sequential order at least one blue-sensitive silver halide emulsion layer, at least one green-sensitive silver halide emulsion layer and at least one red-sensitive silver halide emulsion layer. However, the order may be different from that described above. Furthermore, an infrared sensitive silver halide emulsion layer may be used in place of any one of the above-described blue-, green- and red-sensitive emulsion layers. When the light-sensitive silver halide emulsion layers sensitive to each of the above wavelength regions contain a color coupler capable of forming a dye of color complementary to the color sensitivity of the respective layers, color reproduction may be carried out by subtractive color photography. Usually a yellow coupler is contained in the blue-sensitive silver halide emulsion layer, a magenta coupler in the green-sensitive silver halide emulsion layer and a cyan coupler in the red-sensitive silver halide emulsion layer.

The compounds represented by formula (I) of the present invention are preferably applied to a color light-sensitive material which does not contain a developing agent before color developing, that is, which is processed with a color developing solution containing an aromatic primary amine-based color developing agent and then desilvered to form a color images. Examples of such a color light-sensitive material include color paper, reversal color paper, direct positive color light sensitive materials, color negative films, color positive films, reversal color films, etc. The compounds represented by formula (I) of the present invention are generally applied to color light-sensitive materials having a reflection support (e.g., color paper, reversal color paper) and color light-sensitive materials capable of forming a positive image (e.g., direct positive color light-sensitive materials, color positive films, reversal color films).

Couplers used in combination with the compound represented by formula (I) may be a four-equivalent type or two-equivalent type to silver ion. The couplers may be polymers or oligomers. The couplers may be used either alone or as a mixture of two or more thereof.

Examples of silver halide emulsions and other materials (e.g., additives) for use in the present invention and examples of methods for processing the photographic materials and processing additives are described in the following patent specifications. The materials and techniques described in European Patent No. EP 0,355,660A2 (Japanese Patent Application No. 1-07011) are particularly preferred.

| Photographic constituent element | JP-A-62-215272 | JP-A-2-33144 | EP 0,355,660A2 |
|---|---|---|---|
| Silver halide emulsion | Page 10 right upper column line 6-page 12 left lower column line 5, and the fourth line from the bottom of right lower column of page 12-page 13 left upper column line 17 | Page 28 right upper column line 16-page 29 right lower column line 11, and page 30 lines 2-5 | Page 45 line 53-page 47 line 3 |
| Solvent for silver halide | Page 12 left lower column lines 6-14 and third line from the bottom of left upper column of page 13-the bottom of left lower column of page 18 | — | — |
| Chemical sensitizing agent | Third line from the bottom of left lower column of page 12-fifth line from the bottom of right lower column of page 12, and page 18 right lower column line 1-ninth line from the bottom of right upper column of page 22 | Page 29 right lower column line 12-the bottome therefof | Page 47 lines 4-9 |
| Spectral sensitizing agent (spectral sensitization method) | 8th line from the bottom of right upper column of page 22-the bottom of page 38 | Page 30 left upper column lines 1-13 | Page 47 lines 10-15 |
| Emulsion stabilizer | Page 39 left upper column line 1-the bottom of right upper column of page 72 | Page 30 left upper column line 14-right upper column line 1 | Page 47 lines 16-19 |
| Development accelerator | Page 72 left lower column line 1-page 91 right upper column line 3 | — | — |
| Color coupler (cyan, magenta, yellow couplers) | Page 91 right upper column line 4-page 121 left upper column line 6 | Page 3 right upper column line 14-the bottom of left upper column of page 18, and page 30 right upper column line 6-page 35 right lower column line 11 | Page 4 lines 15-27, page 5 lines 30-the bottom of page 28, page 45 lines 29-31, page 47 line 23-page 63 line 50 |
| Super-sensitizing agent | Page 121 left upper column line 7-page 125 right upper column line 1 | — | — |
| Ultraviolet light absorber | Page 125 right upper column line 2-the bottom of left lower column of page 127 | Page 37 right lower column line 14-page 38 left upper column line 11 | Page 65 lines 22-31 |
| Anti-fading agent (image stabilizer) | Page 127 right lower column line 1-page 137 left lower column line 8 | Page 36 right upper column line 12-page 37 left upper column line 19 | Page 4 line 30-page 5 line 23, page 29 line 1-page 45 line 25, page 45 lines 33-40, page 65 lines 2-21 |
| High boiling and/or low boiling organic solvent | Page 137 left lower column line 9-the bottom of right upper column of page 144 | Page 35 right lower column line 14-4th line from the bottom of left upper column of page 36 | Page 64 lines 1-51 |

-continued

| Photographic constituent element | JP-A-62-215272 | JP-A-2-33144 | EP 0,355,660A2 |
|---|---|---|---|
| Dispersion method of photographic additive | Page 144 left lower column line 1-page 146 right upper column | Page 27 right lower column line 10-the bottom of left upper column of page 28, and page 35 right lower column line 12-page 36 right upper column line 7 | Page 63 line 51-page 64 line 56 |
| Hardening agent | Page 146 right upper column line 8-page 155 left lower column line 4 | — | — |
| Precursor of developing agent | Page 155 left lower column line 5-page 155 right lower column line 2 | — | — |
| Restrainer-releasing compound | Page 155 right lower column lines 3-9 | — | — |
| Support | Page 155 right lower column line 19-page 156 left upper column line 14 | Page 38 right upper column line 18-page 39 left upper column line 3 | Page 66 line 29-page 67 line 13 |
| Constitution of light-sensitive layer | Page 156 left upper column line 15-page 156 right lower column line 14 | Page 28 right upper column lines 1-15 | Page 45 lines 41-52 |
| Dye | Page 156 right lower column line 15-the bottom of right lower column of page 184 | Page 38 left lower column line 12-page 38 right upper column line 7 | Page 66 lines 18-22 |
| Color mixing inhibitor | Page 185 left upper column line 1-page 188 right lower column line 3 | Page 36 right upper column lines 8-11 | Page 64 line 57-page 65 line 1 |
| Gradation controller | Page 188 right lower column lines 4-8 | — | — |
| Anti-staining agent | Page 188 right lower column line 9-page 193 right lower column line 10 | The bottom of left upper column of page 37-page 37 right lower column line 13 | Page 65 line 32-Page 66 line 17 |
| Surfactant | Page 201 left lower column line 1-the bottom of right upper column of page 210 | Page 18 right upper column line 1-the bottom of right lower column of page 24, and 10th line from the bottom of left lower column of page 27-page 27 right lower column line 9 | — |
| Fluorine-containing compound (as antistatic agent, coating aid, lubricant, sticking inhibitor, etc.) | Page 210 left lower column line 1-page 222 left lower column line 5 | Page 25 left upper column line 1-page 27 right lower column line 9 | — |
| Binder (hydrophilic colloid) | Page 222 left lower column line 6-the bottom of left upper column of page 225 | Page 38 right upper column lines 8-18 | Page 66 lines 23-28 |
| Thickener | Page 225 right upper column line 1-page 227 right upper column line 2 | — | — |
| Antistatic agent | Page 227 right upper column line 3-page 230 left upper column line 1 | — | — |
| Polymer latex | Page 230 left upper column line 2-the bottom of page 239 | — | — |
| Matting agent | Page 240 left upper column line 1-the bottom of right upper column of page 240 | — | — |
| Photographic processing method (processing stage, additives, etc.) | Page 3 right upper column line 7-page 10 right upper column line 5 | Page 39 left upper column line 4-the bottom of left upper column of page 42 | Page 67 line 14-page 69 line 28 |

Note: The portions cited in JP-A-62-215272 include the subject matter described in an amendment dated March 16, 1987 and appended to the publication thereof.
Among the color couplers, short wavelength type yellow couplers described in JP-A-63-231451, JP-A-63-123047, JP-A-63-241547, JP-A-1-173499, JP-A-1-213648 and JP-A-1-250944 are preferred as yellow couplers.

In addition to the diphenylimidazole cyan couplers described in JP-A-2-33144, the 3-hydroxypyridine cyan couplers (two-equivalent type coupler formed by introducing a chlorine eliminable group into the four-equivalent type coupler of coupler (42), and couplers (6) and (9) being particularly preferred) described in European Patent EP 0,333,185A2 and cyclic active methylene cyan couplers (couplers 3, 8 and 34 being particularly preferred) described in JP-A-64-32260 are preferably used.

Silver halides for use in the present invention include silver chloride, silver bromide, silver chlorobromide, silver iodochlorobromide and silver iodobromide. However, silver chlorobromide containing substantially no silver iodide and having a silver chloride content of not less than 90 mol%, more preferably not less than 95 mol%, particularly preferably not less than 98 mol% or a silver chloride emulsion is preferred for rapid processing.

Dyes (particularly oxonol dyes) which can be decolorized by processing as described in European Patent EP 0,337,490A2 (pages 27 to 76) are preferably added to the hydrophilic colloid layers of the light-sensitive material of the present invention in an amount such that the light-sensitive material has an optical reflection density of at least 0.70 at 680 nm to thereby improve image sharpness, etc. At least 12% by weight (more preferably at least 14% by weight) of titanium oxide surface treated with a dihydric to tetrahydric alcohol such as trimethylol ethane is preferably incorporated into the water-resistant resin layer of the support.

The light-sensitive material of the present invention preferably contains a dye image preservability-improving compound as described in European Patent EP 0,277,589A2 in the same layer as the couplers, particularly the preferably pyrazoloazole couplers.

Namely, the compound (A) disclosed in European Patent 277,589A2 and/or the compound (B) as disclosed in European Patent 277,589A2 may be used. The compound (A) chemically bonds to an aromatic amine color developing agent remaining in the photographic material after color development, to thereby form a compound which is chemically inert and substantially colorless. The compound (B) chemically bonds to the oxidant of an aromatic amine color developing agent remaining in the photographic material after color development, to thereby form a compound which is chemically inert and substantially colorless. These compounds (A) and (B) may be used alone or in a combination. For example, the use thereof is preferred for preventing the formation of stain or other side effects by reaction of the coupler with color developing agent or the oxidant thereof remaining in the hydrophilic colloid layers during storage after processing.

The hydrophilic colloid layers of the light-sensitive material of the present invention preferably contains the antifungal agents described in JP-A-63-271247 to prevent the growth of mold and bacteria and resulting image deterioration.

Examples of the support for use in the light-sensitive material of the present invention include white polyester supports for display and supports wherein a white pigment-containing layer is provided on the silver halide emulsion layer side of the support. An antihalation layer is preferably provided on the silver halide emulsion layer-coated side of the support or on the back side thereof to improve sharpness. The transmission density of the support is particularly preferably set in the range of from 0.35 to 0.8, to allow enjoyment of the display by reflected light as well as transmitted light.

The light-sensitive material of the present invention may be imagewise exposed to visible light or infrared light. The exposure includes low-illumination exposure and high-illumination short-time exposure. In the latter case, a laser scanning exposure system is preferably used having an exposure time per one pixel of as short as $10^{-4}$ sec.

The band stop filter described in U.S. Pat. No. 4,880,726 is preferably used for exposure, whereby light color mixing is avoided and color reproducibility is greatly improved.

The present invention is now illustrated in greater detail by reference to the following examples which, however, are not to be construed as limiting the present invention in any way.

EXAMPLE 1

16.1 g of yellow coupler Y-1 was weighed, and 16.1 g of high-boiling organic solvent dibutyl phthalate were added thereto. The mixture was dissolved in 24 ml of ethyl acetate. The resulting solution was emulsified and dispersed in 200 g of an 10 wt% aqueous gelatin solution containing 1.5 g of sodium dodecylbenzenesulfonate.

The entire amount of the emulsified dispersion was added to 247 g of a high silver chloride content emulsion (an emulsion having a silver content of 70.0 g/kg and a silver bromide content of 0.5 mol%). The resulting emulsion was coated on a triacetate film base having an undercoat layer in an amount to provide a coating weight of 1.73 g/m² in terms of silver. A gelatin layer as a protective layer was coated on the coated layer in an amount to provide a dry film thickness of about 1.0 μm to prepare a sample 101. The sodium salt of 1-oxy-3,5-dichloro-s-triazine was used as a hardening agent for gelatin.

Samples 102 to 120 were prepared in the same manner as sample 101, except that the combinations of the couplers with the dye image stabilizers (used in an amount of 100 mol% based on the amount of the coupler contained in the coating solution) as indicated in Table 1 were co-emulsified to prepare each of the emulsified dispersions. Coating was conducted in the same manner as in sample 101 to prepare each of samples 102 to 120.

The resulting samples were exposed to white light through a step wedge, and then processed using the following stages.

| Processing Stage | Temperature (°C.) | Time (sec.) |
|---|---|---|
| Color Development | 35 | 45 |
| Bleaching-fixing | 30-35 | 45 |
| Rinse (1) | 30-35 | 20 |
| Rinse (2) | 30-35 | 20 |
| Rinse (3) | 30-35 | 20 |
| Drying | 70-80 | 60 |

Each processing solution had the following composition.

| Color developing solution | |
|---|---|
| Water | 800 ml |
| Ethylenediamine-N,N,N',N'-tetra-methylenephosphonic acid | 1.5 g |
| Potassium bromide | 0.015 g |
| Triethanolamine | 8.0 g |
| Sodium chloride | 1.4 g |
| Potassium carbonate | 25 g |
| N-Ethyl-N-(β-methanesulfonamido-ethyl)-2-methyl-4-aminoaniline sulfate | 5.0 g |
| N,N-Bis(carboxymethyl)hydrazine | 5.5 g |
| Fluorescent brightener (WHITEX 4B, manufactured by Sumitomo Chemical | 1.0 g |

| | |
|---|---|
| Co., Ltd.) | |
| Water to make | 1000 ml |
| pH (25° C.) | 10.05 |
| Bleaching-fixing solution | |
| Water | 400 ml |
| Ammonium thiosulfate (700 g/l) | 100 ml |
| Sodium sulfite | 17 g |
| Ammonium ethylenediaminetetra-acetato ferrate | 55 g |
| Disodium ethylenediaminetetraacetate | 5 g |
| Ammonium bromide | 40 g |
| Water to make | 1000 ml |
| pH (25° C.) | 6.0 |
| Rinsing solution | |
| Ion-exchanged water | |
| (concentration of calcium ion and magnesium ion each reduced to not higher than 3 ppm) | |

The thus-formed dye image on each of the samples to 120 was exposed to a xenon tester (illuminance: 200,000 1×) equipped with an ultraviolet light absorbing filter (manufactured by Fuji Photo Film Co., Ltd.), which removes light having a wavelength of 400 nm or below, for 8 days. Yellow density (stain) in the unexposed areas of each sample was measured, and the retention of yellow density at an initial density of 2.0 was determined.

The measurement was made by using a self-recording densitometer manufactured by Fuji Photo Film Co., Ltd. The results are shown in Table 1.

TABLE 1

| Sample | Coupler | Dye Image Stabilizer | Xe, 200,000 1x, 8 Days | | Remarks |
|---|---|---|---|---|---|
| | | | Stain in Unexposed Area | Retention of Yellow Density (Initial Density: 2.0) (%) | |
| 101 | Y-1 | — | 0.16 | 46 | Comp. Ex. |
| 102 | " | Comparative Compound (a) | 0.17 | 47 | " |
| 103 | " | Comparative Compound (b) | 0.20 | 52 | " |
| 104 | " | Comparative Compound (c) | 0.17 | 55 | " |
| 105 | " | Comparative Compound (d) | 0.23 | 54 | " |
| 106 | " | I-1 | 0.15 | 75 | Invention |
| 107 | " | I-8 | 0.16 | 70 | " |
| 108 | " | I-25 | 0.13 | 82 | " |
| 109 | " | I-41 | 0.15 | 77 | " |
| 110 | Y-10 | — | 0.16 | 43 | Comp. Ex. |
| 111 | " | I-7 | 0.16 | 74 | Invention |
| 112 | " | I-41 | 0.15 | 76 | " |
| 113 | " | I-42 | 0.13 | 84 | " |
| 114 | Y-1 | Comparative Compound (a)* | 0.17 | 50 | Comp. Ex. |
| 115 | Y-16 | — | 0.16 | 39 | " |
| 116 | " | I-25 | 0.13 | 82 | Invention |
| 117 | " | I-41 | 0.13 | 80 | " |
| 118 | Y-17 | — | 0.16 | 48 | Comp. Ex. |
| 119 | " | I-25 | 0.14 | 84 | Invention |
| 120 | " | I-41 | 0.14 | 80 | " |
| 121 | Y-1 | Comparative Compound (e) | 0.20 | 42 | Comp. Ex. |
| 122 | " | Comparative Compound (f) | 0.18 | 52 | " |
| 123 | " | Comparative Compound (g) | 0.22 | 48 | " |

*50 mol % of 1,4-dimethoxy-2,5-di-t-amylbenzene was additionally added to the coating solution.

Comparative Compound (a)

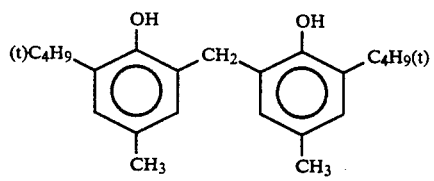

Compound described in JP-A-61-6652 and JP-A-54-70830.

Comparative Compound (b)

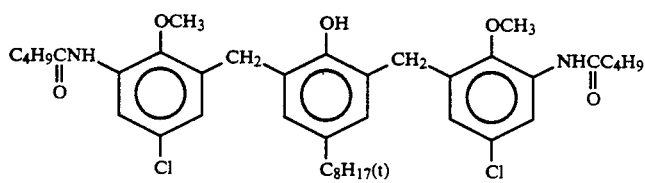

Compound described in JP-A-1-137258.

Comparative Compound (c)

TABLE 1-continued

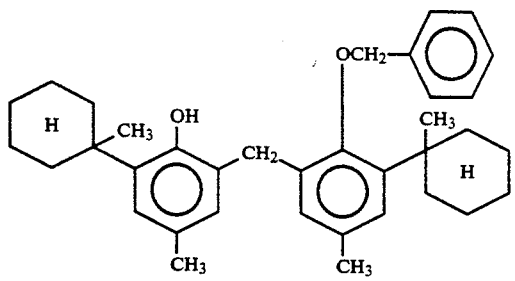

Compound described in JP-A-62-262047.
Comparative Compound (d)

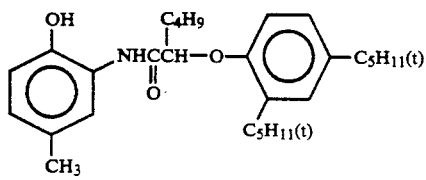

Compound described in JP-A-61-86750.
Comparative Compound (e)

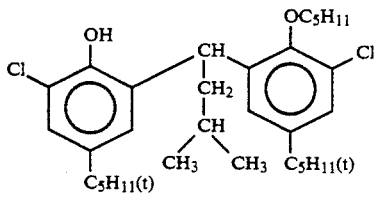

Compound described in JP-A-1-144048.
Comparative Compound (f)

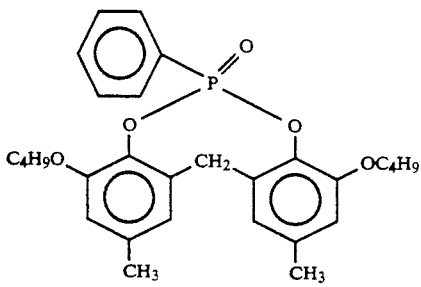

Compound described in JP-A-1-289952 and JP-A-2-8839.
Comparative Compound (g)

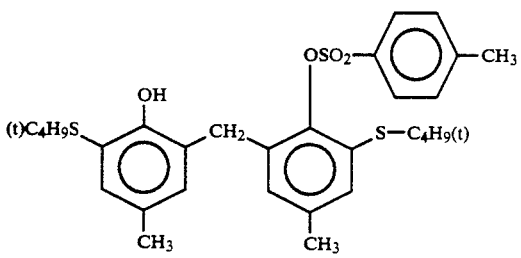

Compound described in JP-A-1-144048.

It is clearly seen from the above noted results that the compounds of the present invention effectively prevent fading of the dye images upon exposure to light, and effectively prevent yellowing of the unexposed areas. These remarkable effects of the present invention are unexpected from comparative testing with conventional anti-fading agents.

EXAMPLE 2

Both sides of a paper support were laminated with polyethylene. The surface of the resulting paper support was subjected to corona discharge treatment. An undercoat layer of gelatin containing sodium dodecylbenzenesulfonate was coated thereon. Furthermore, various photographic constituent layers were coated to prepare a multi-layer color photographic paper having the following layer structure. Coating solutions were prepared in the following manner.

Preparation of Coating Solution for the Fifth Layer 32.0 g of cyan coupler (ExC), 3.0 g of dye image stabilizer (Cpd-2), 2.0 g of dye image stabilizer (Cpd-4), 18.0 g of dye image stabilizer (Cpd-6), 40.0 g of dye image stabilizer (Cpd-7) and 5.0 g of dye image stabilizer (Cpd-8) were dissolved in 50.0 cc of ethyl acetate and 14.0 g of solvent (Solv-6). The resulting solution was added to 500 cc of a 20 wt% aqueous gelatin solution containing 8 cc of sodium dodecylbenzenesulfonate, and the mixture was emulsified and dispersed by means of an ultrasonic homogenizer to prepare an emulsified dispersion. A silver chlorobromide emulsion was separately prepared (cubic; a 1:4 (by mol of Ag) mixture of a large-size emulsion having a mean grain size of 0.58 μm and a small-size emulsion having a mean grain size of 0.45 μm; a coefficient of variation in grain size distribution being 0.09 and 0.11, respectively; 0.06 mol% of AgBr being localized on a part of the surface of the grain in each of the large-size and the small-size emulsions). To the large-size emulsion, was added $0.9 \times 10^{-4}$ mol of the following red-sensitive sensitizing dye E per mol of silver. To the small-size emulsion, there was added $1.1 \times 10^{-4}$ mol of said dye E per mol of silver. The chemical ripening of the emulsion was carried out by using a sulfur sensitizing agent and a gold sensitizing agent. The above emulsified dispersion and the red-sensitive silver chlorobromide emulsion were mixed and dissolved. A coating solution for the fifth layer was thus prepared having the composition given below.

Coating solutions for the first layer to the fourth layer, the sixth layer and the seventh layer were prepared in the same manner as the coating solution for the fifth layer. The sodium salt of 1-oxy-3,5-dichloro-s-triazine was used as the hardening agent for gelatin in each layer.

To each layer were added Cpd-10 and Cpd-11 in a total amount of 25.0 mg/m² and 50.0 mg/m², respectively.

The following spectral sensitizing dyes were used for the silver chlorobromide emulsion of each light-sensitive emulsion layer.

Blue-sensitive Emulsion Layer

Sensitizing Dye A

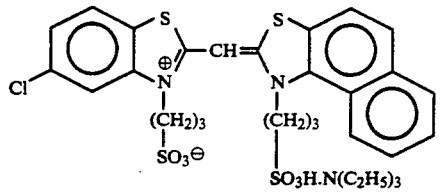

and Sensitizing Dye B

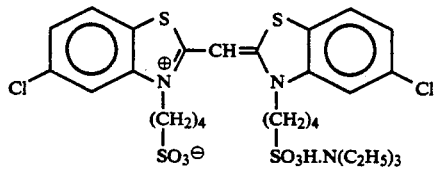

($2.0 \times 10^{-4}$ mol of each dye being added to the large-size emulsion, and $2.5 \times 10^{-4}$ mol of each dye being added to the small-size emulsion, each amount being per mol of silver halide)

Green-sensitive Emulsion Layer

Sensitizing Dye C

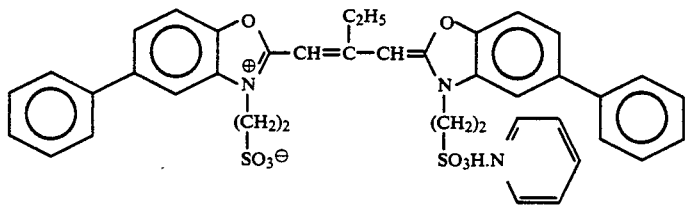

($4.0 \times 10^{-4}$ mol being added to the large-size emulsion, and $5.6 \times 10^{-4}$ mol being added to the small-size emulsion, each amount being per mol of silver halide)

and Sensitizing Dye D

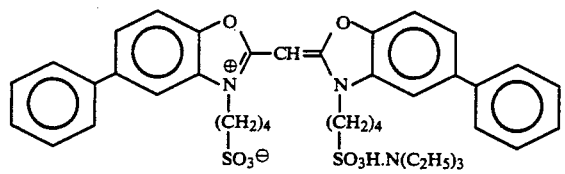

($7.0 \times 10^{-5}$ mol being added to the large-size emulsion, and $1.0 \times 10^{-5}$ mol being added to the small-size emulsion, each amount being per mol of silver halide)

Red-sensitive Emulsion Layer

Sensitizing Dye E

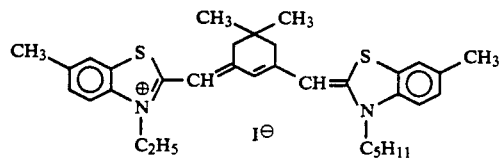

($0.9 \times 10^{-4}$ mol being added to the large-size emulsion, and $1.1 \times 10^{-4}$ mol being added to the small-size emulsion, each amount being per mol of silver halide)

Furthermore, $2.6\times10^{-3}$ mol of the following compound per mol of silver halide was added.

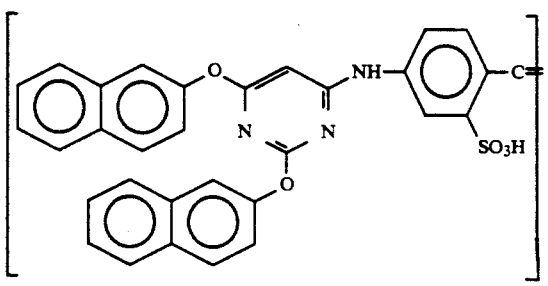

Additionally, $8.5\times10^{-5}$ mol, $7.7\times10^{-4}$ mol and $2.5\times10^{-4}$ mol of 1-(5-methylureidophenyl)-5-mercaptotetrazole were added to the blue-sensitive emulsion layer, the green-sensitive emulsion layer and the red-sensitive emulsion layer, respectively, each in an amount per mol of silver halide.

Furthermore, $1\times10^{-4}$ mol and $2\times10^{-4}$ mol of 4-hydroxy-6-methyl-1,3,3a,7-tetrazaindene were added to the blue-sensitive emulsion layer and the green-sensitive emulsion layer, respectively, each in an amount per mol of silver halide.

The following dyes (parenthesized numerals being coating weights) were added to the emulsion layers to prevent irradiation.

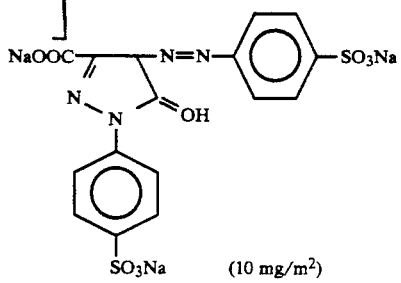

(10 mg/m²)

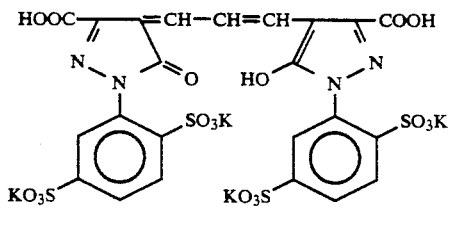

(10 mg/m²)

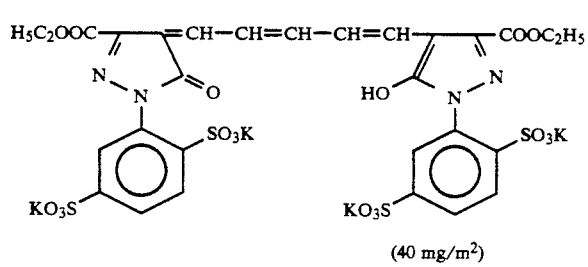

(40 mg/m²)

and

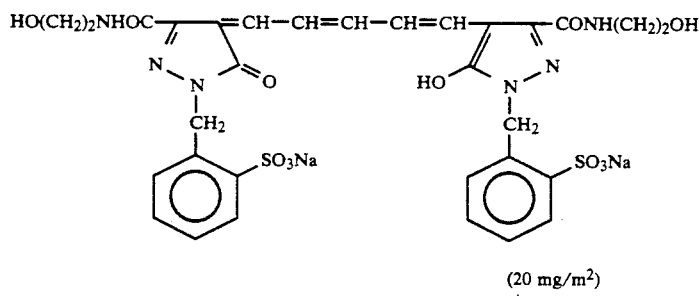

(20 mg/m²)

Layer Structure

Each layer had the following composition. Numerals represent coating weights (g/m²). The amounts of the silver halide emulsions are represented by coating weight in terms of silver.

Support

Polyethylene-laminated paper (polyethylene on the first layer side contained a white pigment (TiO₂) and a bluing dye (ultramarine))

| | |
|---|---|
| First Layer (Blue-sensitive Emulsion Layer) | |
| Silver chlorobromide emulsion (cubic; a 3:7 (by mol of Ag) mixture of a large-size emulsion having a mean grain size of 0.88 μm and a small-size emulsion having a mean grain size of 0.70 μm; coefficient of variation in grain size distribution of 0.08 and 0.10, respectively; 0.3 mol % of silver bromide localized on a part of the surface of the grain in each of the large-size emulsion and the small-size emulsion) | 0.30 |
| Gelatin | 1.86 |
| Yellow coupler (ExY) | 0.82 |
| Dye image stabilizer (Cpd-1) | 0.19 |
| Solvent (Solv-3) | 0.18 |
| Solvent (Solv-7) | 0.18 |
| Dye image stabilizer (Cpd-7) | 0.06 |
| Second Layer (Color Mixing Inhibiting Layer) | |
| Gelatin | 0.99 |
| Color mixing inhibitor (Cpd-5) | 0.08 |
| Solvent (Solv-1) | 0.16 |
| Solvent (Solv-4) | 0.08 |
| Third Layer (Green-sensitive Emulsion Layer) | |
| Silver chlorobromide emulsion (cubic; a 1:3 (by mol of Ag) mixture of a large-size emulsion having a mean grain size of 0.55 μm and a small-size emulsion having a mean grain size of 0.39 μm; coefficient of variation in grain size distribution of 0.10 and 0.08, respectively; 0.8 mol % of AgBr localized on a part of the surface of the grain in each of the large-size emulsion and the small-size emulsion) | 0.12 |
| Gelatin | 1.24 |
| Magenta coupler (ExM) | 0.23 |
| Dye image stabilizer (Cpd-2) | 0.03 |
| Dye image stabilizer (Cpd-3) | 0.16 |
| Dye image stabilizer (Cpd-4) | 0.02 |
| Dye image stabilizer (Cpd-9) | 0.02 |
| Solvent (Solv-2) | 0.40 |
| Fourth Layer (Ultraviolet Light Absorbing Layer) | |
| Gelatin | 1.58 |
| Ultraviolet light absorber (UV-1) | 0.47 |
| Color mixing inhibitor (Cpd-5) | 0.05 |
| Solvent (Solv-5) | 0.24 |
| Fifth Layer (Red-sensitive Emulsion Layer) | |
| Silver chlorobromide emulsion (cubic; a 1:4 (by mol of Ag) mixture of a large-size emulsion having a mean grain size of 0.58 μm and a small-size emulsion having a mean grain size of 0.45 μm; coefficient of variation in grain size distribution of 0.09 and 0.11, respectively; 0.6 mol % of AgBr localized on a part of the surface of the grain in each of the large-size emulsion and the small-size emulsion) | 0.23 |
| Gelatin | 1.34 |
| Cyan coupler (ExC) | 0.32 |
| Dye image stabilizer (Cpd-2) | 0.03 |
| Dye image stabilizer (Cpd-4) | 0.02 |
| Dye image stabilizer (Cpd-6) | 0.18 |
| Dye image stabilizer (Cpd-7) | 0.40 |
| Dye image stabilizer (Cpd-8) | 0.05 |
| Solvent (Solv-6) | 0.14 |
| Sixth Layer (Ultraviolet Light Absorbing Layer) | |
| Gelatin | 0.53 |
| Ultraviolet light absorber (UV-1) | 0.16 |
| Color mixing inhibitor (Cpd-5) | 0.02 |
| Solvent (Solv-5) | 0.08 |
| Seventh Layer (Protective Layer) | |
| Gelatin | 1.33 |
| Acrylic-modified polymer of polyvinyl alcohol (a degree of modification: 17%) | 0.17 |
| Liquid paraffin | 0.03 |

Yellow Coupler (ExY):

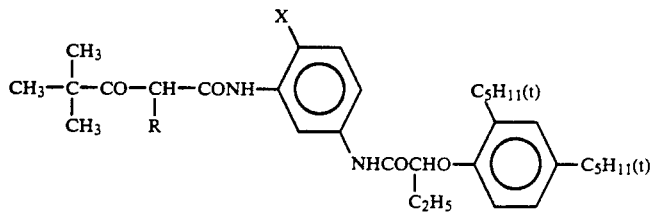

-continued
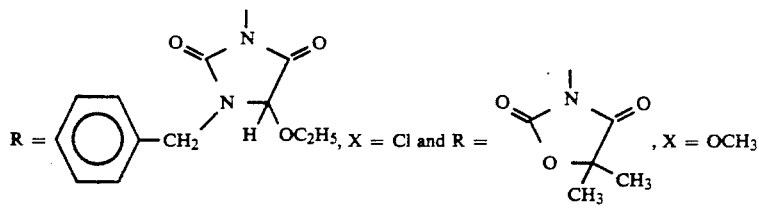
1:1 mixture (by mol)
Magenta Coupler (ExM):
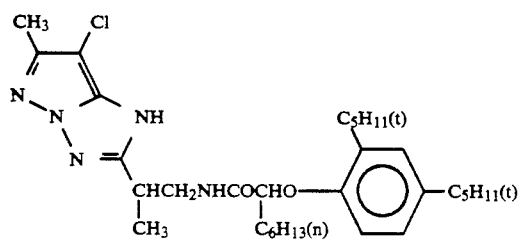
Cyan Coupler (ExC):
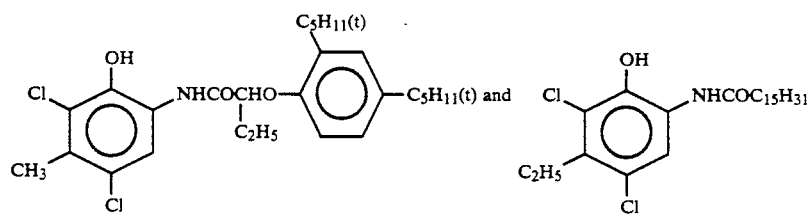
1:1 mixture (by mol)
Dye Image Stabilizer (Cpd-1):
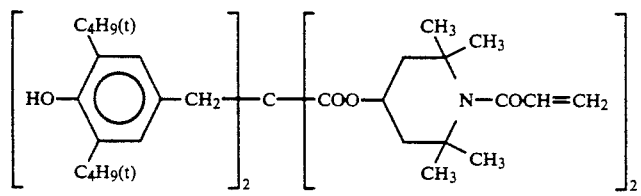
Dye Image Stabilizer (Cpd-2):
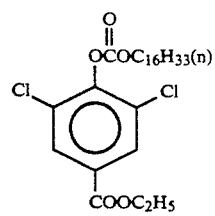
Dye Image Stabilizer (Cpd-3):
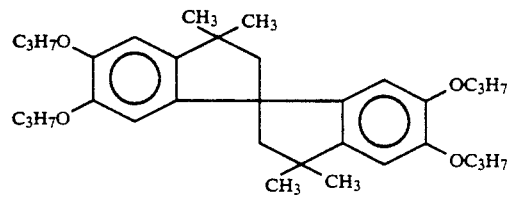
Dye Image Stabilizer (Cpd-4):

-continued
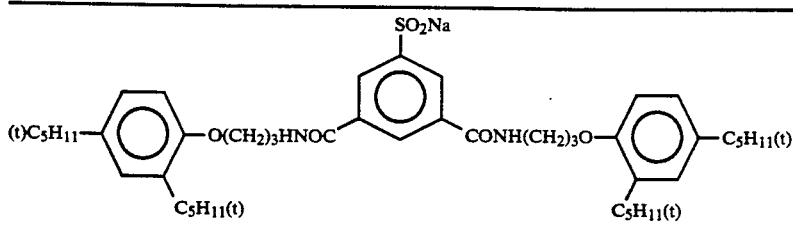
Color Mixing Inhibitor (Cpd-5):
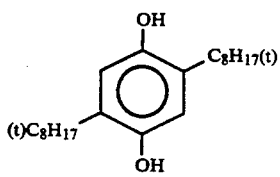
Dye Image Stabilizer (Cpd-6):
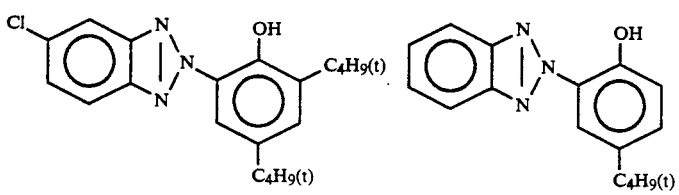
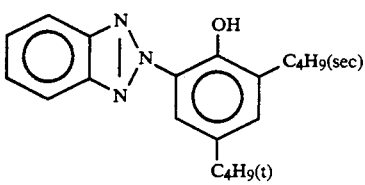
2:4:4 mixture (by weight)
Dye Image Stabilizer (Cpd-7):
Average MW = 60,000
Dye Image Stabilizer (Cpd-8):
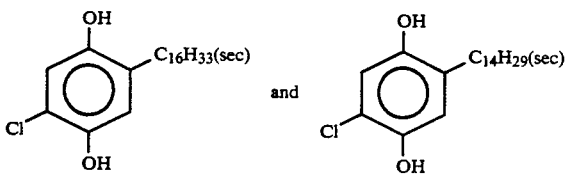
1:1 mixture (by weight)
Dye Image Stabilizer (Cpd-9):
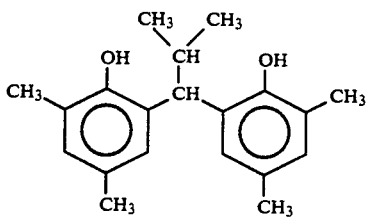
Antiseptic (Cpd-10):

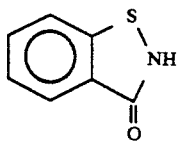
Antiseptic (Cpd-11):
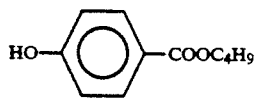
Ultraviolet Light Absorber (UV-1):
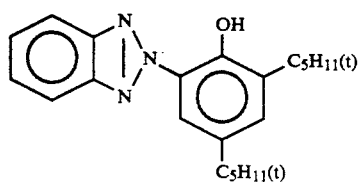   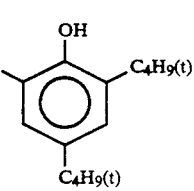
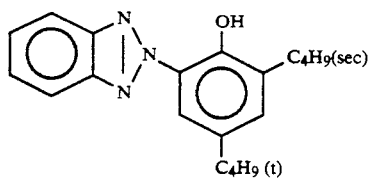
4:2:4 mixture (by weight)
Solvent (Solv-1):
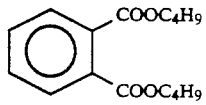
Solvent (Solv-2):
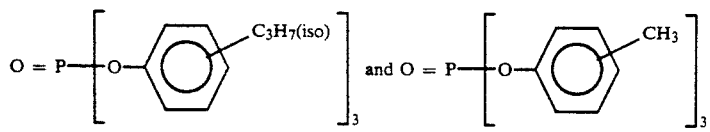
1:1 mixture (by volume)
Solvent (Solv-3):
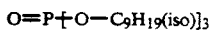
Solvent (Solv-4):
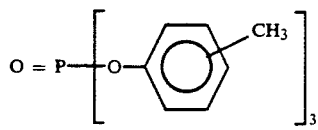
Solvent (Solv-5):
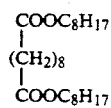

-continued

Solvent (Solv-6):

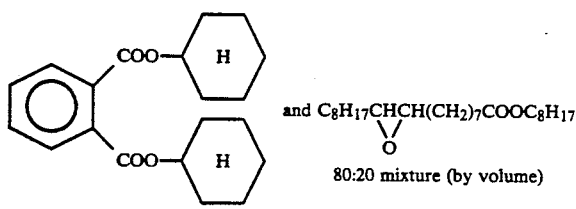

and $C_8H_{17}CHCH(CH_2)_7COOC_8H_{17}$
  \\/
   O

80:20 mixture (by volume)

Solvent (Solv-7):

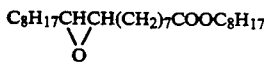

$C_8H_{17}CHCH(CH_2)_7COOC_8H_{17}$
  \\/
   O

The samples thus prepared were exposed using a sensitometer (color temperature of light source: 3200° K., FWH Type manufactured by Fuji Photo Film Co., Ltd.) and each sample was subjected to gradation exposure through a three-color separation filter for sensitometery. The exposure time was 0.1 sec., and exposure was carried out in an exposure amount of 250 CMS.

The exposed samples were subjected to continuous processing (running test) using a paper processor and processing solutions having the following compositions in the following processing stages, until the replenishment amount reached twice the tank capacity of the color development.

| Processing Stage | Temperature (°C.) | Time (sec.) | Replenisher(*) (ml) | Tank Capacity (l) |
|---|---|---|---|---|
| Color Development | 35 | 45 | 161 | 17 |
| Bleach-fixing | 30–35 | 45 | 215 | 17 |
| Rinse (1) | 30–35 | 20 | — | 10 |
| Rinse (2) | 30–35 | 20 | — | 10 |
| Rinse (3) | 30–35 | 20 | 350 | 10 |
| Drying | 70–80 | 60 | | |

(*)Replenishment rate per m² of light-sensitive material processed.
The rinse was carried out using a three tank countercurrent system of from (3) to (2) and from (2) to (1).

Each processing solution had the following composition.

| | Tank Solution | Replenisher |
|---|---|---|
| Color Developing Solution | | |
| Water | 800 ml | 800 ml |
| Ethylenediamine-N,N,N',N'-tetramethylenephosphonic acid | 1.5 g | 2.0 g |
| Potassium bromide | 0.015 g | |
| Triethanolamine | 8.0 g | 12.0 g |
| Sodium chloride | 1.4 g | |
| Potassium carbonate | 25 g | 25 g |
| N-Ethyl-N-(β-methanesulfon-amidoethyl)-3-methyl-4-amino-aniline sulfate | 5.0 g | 7.0 g |
| N,N-bis(carboxymethyl)-hydrazine | 4.0 g | 5.0 g |
| Monosodium salt of N,N-di-(sulfoethyl)hydroxylamine | 4.0 g | 5.0 g |
| Fluorescent brightener (WHITEX 4B manufactured by Sumitomo Chemical Co., Ltd.) | 1.0 g | 2.0 g |
| Water to make | 1000 ml | 1000 ml |
| pH (25° C.) | 10.05 | 10.45 |
| Bleaching-fixing Solution | | |

Tank solution and replenisher had the same composition.

| | |
|---|---|
| Water | 400 ml |
| Ammonium thiosulfate (70 wt %) | 100 ml |
| Sodium sulfite | 17 g |
| Ammonium ethylenediaminetetraacetato ferrate | 55 g |
| Disodium ethylenediaminetetraacetate | 5 g |
| Ammonium bromide | 40 g |
| Water to make | 1000 ml |
| pH (25° C.) | 6.0 |

Rinsing Solution

The tank solution and replenisher had the same composition.
Ion-exchanged water
(concentration of each of calcium ion and magnesium ion reduced to not more than 3 ppm)

The thus-obtained sample was referred to as sample 1A. Samples 2A to 8A were prepared in the same manner as sample 1A, except that the combinations of the coupler with the dye image stabilizers (dye image stabilizers Cpd-1 and Cpd-7 being added) as indicated in Table 2 were co-emulsified in place of the combination of the yellow coupler with the dye image stabilizer used in the first layer of sample 1A. The dye image stabilizers were used in an equimolar amount based on the amount of yellow coupler. The comparative compounds used were the same as those used in Example 1.

The thus-obtained dye images formed on each of the samples were subjected to a fading test. The fade inhibiting effect was evaluated by determining the retention of yellow density at an initial density of 2.0 after exposing the dye image to a xenon tester (illuminance: 200,000 1×) for 10 days.

The measurements were made using a self-recording densitometer manufactured by Fuji Photo Film Co., Ltd. The results are shown in Table 2.

TABLE 2

| Sample | Coupler | Dye Image Stabilizer | Xe, 200,000 lx, 10 Days | | Remarks |
| --- | --- | --- | --- | --- | --- |
| | | | Stain in Unexposed Area | Retention of Yellow Density (Initial Density: 2.0) (%) | |
| 1A | ExY | — | 0.14 | 66 | Comp. Ex. |
| 2A | " | Comparative Compound (a) | 0.17 | 64 | " |
| 3A | " | Comparative Compound (b) | 0.18 | 70 | " |
| 4A | " | I-5 | 0.13 | 85 | Invention |
| 5A | " | I-29 | 0.12 | 84 | " |
| 6A | Y-10 | — | 0.16 | 51 | Comp. Ex. |
| 7A | " | I-25 | 0.14 | 82 | Invention |
| 8A | " | I-27 | 0.14 | 80 | " |

It is clearly seen from the results of Table 2 that the samples containing the compounds of formula (I) of the present invention provided the same excellent effect as in Example 1, even when applied to a photographic material in the form of a multi-layer structure.

EXAMPLE 3

Samples were prepared in the same manner as sample 101 of Example 1 of JP-A-2-854, except that 25 mol% (based on the amount of the coupler used in each of the third, fourth and fifth layers of the sample 101) of the compound I-1, I-5, I-29 or I-30 of the present invention was co-emulsified and used in each of the third, fourth and fifth layers.

Furthermore, additional samples were prepared in the same manner as sample 101 of Example 1 of JP-A-2-854, except that 25 mol% (based on the amount of the coupler used in each of the 12th and 13th layers of sample 101) of the compound I-5, I-25, I-29 or I-30 of the present invention was co-emulsified and added to each of the 12th and 13th layers.

In the same manner as in Example 1 of JP-A-2-854, these samples were exposed, developed and subjected to the fading test. The samples of the present invention provided an excellent fade inhibiting effect and good photographic characteristics.

It was thus demonstrated that the compounds of the present invention are effective even when used in a light-sensitive material of the type described in JP-A-2-854.

EXAMPLE 4

A sample was prepared in the same manner as the color photographic material of Example 2 of JP-A-1-158431, except that an equimolar amount (based on the amount of the coupler) of the compound I-5, I-25, I-29 or I-30 of the present invention was added to each of the third and fourth layers of the color photographic material.

A sample was prepared in the same manner as the color photographic material of Example 2 of JP-A-1-158431, except that an equimolar amount of the compound I-1, I-5, I-29 or I-30 of the present invention was used in place of Cpd-6 used in each of the 11th and 12th layers of the color photographic material.

In the same manner as in Example 2 of JP-A-1-158431, these samples were exposed, developed and subjected to a fading test. The photographic characteristics thereof were evaluated. It was determined that the samples of the present invention provided an excellent fade inhibiting effect and good photographic characteristics.

It was thus demonstrated that the compounds of the present invention are effective even when used in a light-sensitive material of the type described in JP-A-1-158431.

EXAMPLE 5

A sample 201 was prepared in the same manner as sample 101 of Example 1, except that 9.8 g of cyan coupler (C-7) was used in place of the yellow coupler used in sample 101 of Example 1.

Samples 202 to 211 were prepared in the same manner as sample 201, except that the combinations of the couplers with the dye image stabilizers (in an amount of 100 mol% based on the amount of the coupler) were co-emulsified. The comparative examples used were the same as those used in Example 1.

The thus-obtained samples were exposed and developed in the same manner as in Example 1.

The thus-formed dye images on each of the samples 201 to 211 were subjected to a xenon tester (illuminance: 200,000 1×) equipped with an ultraviolet light absorbing filter (manufactured by Fuji Photo Film Co., Ltd.), which removes light having a wavelength of 400 nm or below, for 8 days. Yellow density (stain) in the unexposed areas of each sample was measured, and the retention of yellow density at an initial density of 2.0 was determined.

Furthermore, each of the samples 201 to 211 having a dye image formed thereon was stored at 100° C. for 16 days. Yellow density in the unexposed areas of each sample was measured, and the retention of cyan density of an initial density of 2.0 was determined.

The measurements were made by using a self-recording densitometer manufactured by Fuji Photo Film Co., Ltd. The results are shown in Table 3.

TABLE 3

| Sample | Coupler | Dye Image Stabilizer | Xe, 200,000 lx, 8 Days | | Remarks |
| --- | --- | --- | --- | --- | --- |
| | | | Stain in Unexposed Area | Retention of Cyan Density (Initial Density: 2.0) (%) | |
| 201 | C-7 | — | 0.18 | 48 | Comp. Ex. |
| 202 | " | Comparative Compound (a) | 0.20 | 50 | " |
| 203 | " | Comparative Compound (c) | 0.19 | 48 | " |
| 204 | " | I-5 | 0.16 | 80 | Invention |
| 205 | " | I-7 | 0.18 | 74 | " |
| 206 | " | I-9 | 0.18 | 71 | " |

TABLE 3-continued

| | | | Xe, 200,000 lx, 8 Days | | |
|---|---|---|---|---|---|
| Sample | Coupler | Dye Image Stabilizer | Stain in Unexposed Area | Retention of Cyan Density (Initial Density: 2.0) (%) | Remarks |
| 207 | " | I-27 | 0.18 | 78 | " |
| 208 | C-11 | — | 0.22 | 32 | Comp. Ex. |
| 209 | " | Comparative Compound (a) | 0.24 | 30 | " |
| 210 | " | I-41 | 0.20 | 70 | Invention |
| 211 | " | I-42 | 0.18 | 78 | " |

It is clearly seen from the above noted results that the compounds of the present invention effectively prevent fading of cyan dye images upon exposure to light and heat. Furthermore, it is clearly seen that the compounds of the present invention effectively prevent the unexposed areas from yellowing.

EXAMPLE 6

Samples 2B to 4B were prepared in the same manner as sample 1A of Example 2, except that the combinations of the cyan coupler with the dye image stabilizers (added in an amount of 100 mol% based on the amount of the cyan coupler) as indicated in Table 4 were co-emulsified in place of the combination of the cyan coupler with the dye image stabilizers used in the fifth layer of sample 2A.

The thus-obtained samples were exposed and developed in the same manner as in Example 2. Each sample having a dye image formed thereon was subjected to a fading test. The fade inhibiting effect of the samples was evaluated in the following manner. After the samples were exposed to a xenon tester (illuminance: 200,000 1×) for 12 days, the retention of cyan density at an initial density of 2.0 was determined. Furthermore, after the samples were stored at 100° C. for 400 hours, the retention of cyan density at an initial density of 2.0 was determined.

The measurements were made using a self-recording densitometer manufactured by Fuji Photo Film Co., Ltd. The results are shown in Table 4.

TABLE 4

| | | | Retention of Cyan Density (Initial Density: 2.0) | | |
|---|---|---|---|---|---|
| Sample | Coupler | Dye Image Stabilizer | Xe, 200,000 1x 12 Days (%) | 100° C. 4 Hours (%) | Remarks |
| 1A | ExC | — | 70 | 74 | Comp. Ex. |
| 2B | " | Comparative Compound (a) | 65 | 72 | " |
| 3B | " | I-5 | 84 | 88 | Invention |
| 4B | " | I-40 | 78 | 86 | " |

It is clearly seen from the above noted results that the compounds of the present invention effectively prevent cyan dye images from fading upon exposure to light and heat, even when the photographic material is in the form of a multi-layer structure.

In view of the above experimentation, it is clearly seen that the compounds of formula (I) of the present invention effectively improve the fastness of yellow couplers and cyan couplers to light in comparison with conventional anti-fading agents.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon one or more hydrophilic colloid layers, at least one layer of which is a light-sensitive silver halide emulsion layer containing in the same layer a color coupler selected from the group consisting of a yellow coupler and a cyan coupler and at least one compound represented by formula (I-A):

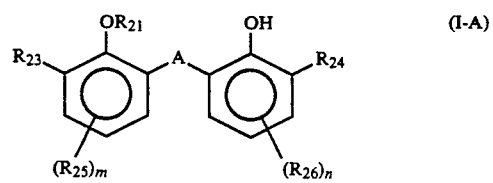

wherein A represents a single bond, —O—, —S(O)$_p$—, —N(R$_{27}$)— or —(C(R$_{28}$)(R$_{29}$))$_T$—; R$_{21}$ represents a hydrogen atom, an aliphatic group, —C(O)—R$_{33}$, —S(O)$_2$—R$_{33}$, —P(R$_{33}$)(R$_{34}$) or —P(O)(R$_{33}$)(R$_{34}$); R$_{23}$ and R$_{24}$ each represents an aliphatic acylamino group, an aromatic acylamino group, an aliphatic carbamoylamino group, an aromatic carbamoylamino group, an aliphatic sulfamoylamino group, an aromatic sulfamoylamino group, an imido group, an aliphatic oxycarbonylamino group, an N-alkylated aliphatic sulfonamido group or an N-alkylated aromatic sulfonamido group; R$_{25}$ and R$_{26}$ each represents an aromatic group, a heterocyclic group, an aromatic oxy group, an aromatic thio group, an aliphatic acyl group, an aromatic acyl group, an aliphatic oxycarbonyl group, an aromatic oxycarbonyl group, an aliphatic acylamino group, an aromatic acylamino group, an aliphatic sulfonamido group, an aromatic sulfonamido group, an imido group, an aliphatic acyloxy group, an aromatic acyloxy group, an aliphatic sulfonyl group, an aromatic sulfonyl group, an aliphatic sulfonyloxy group, an aromatic sulfonyloxy group, an aliphatic oxycarbonylamino group, an aromatic oxycarbonylamino group, a carbamoylamino group, a sulfamoylamino group, a carbamoyl group, a sulfamoyl group, a group represented by the following formula:

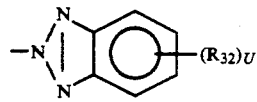

or an aliphatic group, m and n each represents an integer of 1 to 3 and when any of m and n are 2 or 3, the two or three $R_{25}$ and $R_{26}$ groups may be the same or different; $R_{21}$ and $R_{23}$, $R_{23}$ and $R_{25}$ or $R_{24}$ and $R_{26}$ may be combined together to form a five-membered to eight-membered ring; $R_{27}$ represents hydrogen atom, an aliphatic group, an aliphatic acyl group, an aromatic acyl group, an aliphatic sulfonyl group, an aromatic sulfonyl group, an aliphatic oxycarbonyl group or an aromatic oxycarbonyl group; $R_{28}$ and $R_{29}$ each represents a hydrogen atom, an aliphatic group or an aromatic group; $R_{32}$ has the same meaning as $R_{25}$; $R_{33}$ and $R_{34}$ each represents an aliphatic group, an aromatic group, an aliphatic oxy group or an aromatic oxy group; p and U each represents 0, 1 or 2; and T represents 1 or 2 and when T is 2, the two $R_{28}$ and $R_{29}$ groups may be the same or different.

2. A silver halide color photographic material as in claim 1, wherein the yellow coupler is represented by formula (Y):

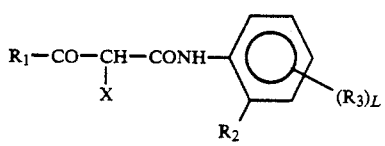

wherein $R_1$ represents a tertiary alkyl group, an aryl group, a substituted amino group or a nitrogen-containing heterocyclic ring bonded to the residue through a nitrogen atom; $R_2$ represents hydrogen atom, a halogen atom, an alkoxy group, an aryloxy group, an alkyl group or a dialkylamino group; $R_3$ represents a substituent group capable of bonding to the benzene ring; X represents a hydrogen atom or a group which can be eliminated by a coupling reaction with the oxidant of an aromatic primary amino developing agent; and L represents an integer of 0 to 4 and when L is 2 or greater, two or more $R_3$ groups may be the same or different.

3. A silver halide color photographic material as in claim 2, wherein $R_1$ in formula (Y) is a t-butyl group, a 1-alkylcyclopropyl group or an indolinyl group.

4. A silver halide color photographic material as in claim 1, wherein the yellow coupler is contained in an amount of 0.001 to 1 mol per mol of light-sensitive silver halide in the same layer.

5. A silver halide color photographic material as in claim 1, wherein the cyan coupler is represented by formula (C-I) or (C-II):

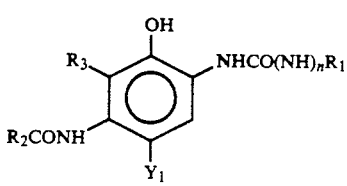

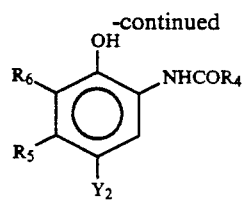

wherein $R_1$, $R_2$ and $R_4$ each represents an aliphatic group, an aromatic group or a heterocyclic group; $R_3$, $R_5$ and $R_6$ each represents a hydrogen atom, a halogen atom, an aliphatic group, an aromatic group or an acylamino group, or $R_3$ is a non-metallic atomic group forming a nitrogen-containing five-membered or six-membered heterocyclic ring together with $R_2$; $Y_1$ and $Y_2$ each represents a hydrogen atom or a group which is eliminated by the coupling reaction with the oxidant of an aromatic primary amino developing agent; and n represents 0 or 1.

6. A silver halide color photographic material as in claim 1, wherein the cyan coupler is contained in an amount of 0.001 to 1 mol per mol of light-sensitive silver halide in the same layer.

7. A silver halide color photographic material as in claim 1, wherein the compounds represented by formula (I-A) are represented by formula (I-B):

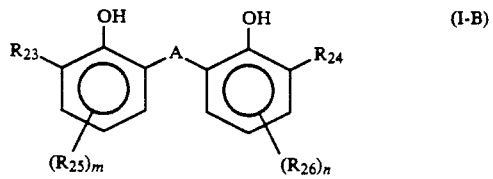

wherein $R_{23}$, $R_{24}$, $R_{25}$, $R_{26}$, A, m and n are as defined in formula (I).

8. A silver halide color photographic material as in claim 1, wherein A in formula (I-A) is —C($R_{28}$)($R_{29}$)— or —O—, in which $R_{28}$ and $R_{29}$ are as defined in formula (I).

9. A silver halide color photographic material as in claim 8, wherein A is —C($R_{28}$)($R_{29}$)—, in which one $R_{28}$ and $R_{29}$ is a hydrogen atom and the other is an aliphatic group.

10. A silver halide color photographic material as in claim 1, wherein $R_{23}$ and $R_{24}$ each is an alkylacylamino group, an alkylcarbamoylamino group or an alkoxycarbonylamino group.

11. A silver halide color photographic material as in claim 1, wherein $R_{25}$ and $R_{26}$ in formula (I-A) each is an aliphatic acylamino group, an aromatic acylamino group, an aliphatic carbamoylamino group, an aromatic carbamoylamino group, an aliphatic sulfamoylamino group, an aromatic sulfamoylamino group, an imido group, an aliphatic oxycarbonylamino group, an N-alkylated aliphatic sulfonamido group, an N-alkylated aromatic sulfonamido group or an aliphatic group.

12. A silver halide color photographic material as in claim 11, wherein $R_{25}$ and $R_{26}$ in formula (I-A) each is an alkylacylamino group, an alkylcarbamoylamino group, an alkoxycarbamoylamino group or an aliphatic group.

13. A silver halide color photographic material as in claim 11, wherein $R_{25}$ and $R_{26}$ in formula (I-A) each is an aliphatic group.

14. A silver halide color photographic material as in claim 13, wherein $R_{25}$ and $R_{26}$ each is a straight-chain alkyl group.

15. A silver halide color photographic material as in claim 1, wherein the compound of formula (I-A) is contained in an amount of from 0.5 to 300 mol% based on the content of the coupler in the same layer.

* * * * *